US008883516B2

(12) United States Patent
Manetto et al.

(10) Patent No.: US 8,883,516 B2
(45) Date of Patent: Nov. 11, 2014

(54) CLICK CHEMISTRY ON HETEROGENEOUS CATALYSTS

(75) Inventors: Antonio Manetto, München (DE); Philipp Mathias Edwin Gramlich, Gilching (DE); Simon Warncke, München (DE)

(73) Assignee: Baseclick GmbH, Tutzing (DE)

( * ) Notice: Subject to any disclaimer, the term of this patent is extended or adjusted under 35 U.S.C. 154(b) by 43 days.

(21) Appl. No.: 13/263,401

(22) PCT Filed: Apr. 8, 2010

(86) PCT No.: PCT/EP2010/054645
§ 371 (c)(1),
(2), (4) Date: Jan. 3, 2012

(87) PCT Pub. No.: WO2010/115957
PCT Pub. Date: Oct. 14, 2010

(65) Prior Publication Data
US 2012/0100633 A1    Apr. 26, 2012

Related U.S. Application Data

(60) Provisional application No. 61/167,981, filed on Apr. 9, 2009.

(30) Foreign Application Priority Data

Apr. 9, 2009 (EP) .................................. 09005239

(51) Int. Cl.
| | |
|---|---|
| B01J 23/72 | (2006.01) |
| G01N 33/53 | (2006.01) |
| C07H 1/00 | (2006.01) |
| C07K 9/00 | (2006.01) |
| C07D 249/04 | (2006.01) |
| B01J 21/18 | (2006.01) |

(52) U.S. Cl.
CPC .............. *C07D 249/04* (2013.01); *B01J 21/18* (2013.01); *B01J 23/72* (2013.01)
USPC .......... 436/501; 536/25.3; 530/322; 422/129; 422/524

(58) Field of Classification Search
None
See application file for complete search history.

(56) References Cited

FOREIGN PATENT DOCUMENTS

| WO | WO 2006/117161 | 11/2006 |
|---|---|---|
| WO | WO 2008/052775 | 5/2008 |

OTHER PUBLICATIONS

A print-out from http://en.wikipedia.org/wiki/Heterogeneous_catalysis retrieved on Jul. 9, 2013.*
Abstract of Snezhkova et al., "DNA-coated carbon adsorbents experimental assessment and results of severe psoriasis treatment," Biomater Artif Cells Immobilization Biotechnol., 1992, vol. 20, No. 5, pp. 1201-1221.*
Bouillon et al., "Microwave assisted 'click' chemistry for the synthesis of multiple labeled-carbohydrate oligonucleotides on solid support", Journal of Organic Chemistry, Jun. 9, 2006, vol. 71, No. 12, pp. 4700-4702.
Devaraj et al., "Chemoselective covalent coupling of oligonucleotide probes to self-assembled monolayers", Journal of the American Chemical Society, Jun. 2005, vol. 127, No. 24, pp. 8600-8601.
Gramlich et al., "Postsynthetic DNA modification through the copper-catalyzed azide-alkyne cycloaddition reaction", Angewandte Chemie (International edition in English), 2008, vol. 47, No. 44, pp. 8350-8358.
Lipshutz et al., "Heterogeneous copper-in-charcoal-catalyzed click chemistry", Angewandte Chemie (International edition in English), Dec. 11, 2006, vol. 45, No. 48, pp. 8235-8238.
Lutz et al., "Efficient construction of therapeutics, bioconjugates, biomaterials and bioactive surfaces using azide-alkyne 'click' chemistry", Advanced Drug Delivery Reviews, Jun. 10, 2008, vol. 60, No. 9, pp. 958-970.
Norgren et al., "On-resin click-glycoconjugation of peptoids", Synthesis, Jan. 9, 2009, No. 3, pp. 488-494.
Sharghi et al., "Copper nanoparticles on charcoal for multicomponent catalytic synthesis of 1,2,3-triazole derivatives from benzyl halides or alkyl halides, terminal alkynes and sodium azide in water as a 'green' solvent", Adv. Synth. Catal., Jan. 12, 2009, vol. 351, pp. 207-218.
Turner et al., "Click chemistry as a macrocyclization tool in the solid-phase synthesis of small cyclic peptides", Org. Lett., 2007, vol. 9, No. 24, pp. 5011-5014.
Urankar et al., "Concise and diversity-oriented synthesis of ligand arm-functionaiized azoamides", Journal of Combinatorial Chemistry, 2008, vol. 10, No. 6, pp. 981-985.
Yim et al., "Versatile conjugation of octreotide to dendrimers by cycloaddition ('click') chemistry to yield high-affinity multivalent cyclic peptide dendrimers", Bioconjugate Chemistry, ACS, Washington, Jul. 1, 2009, vol. 20, No. 7, pp. 1323-1331.
International Search Report, PCT/EP2010/054645, completed Jul. 13, 2010.
International Preliminary Report on Patentability, PCT/EP2010/054645, completed Jul. 21, 2011.

* cited by examiner

*Primary Examiner* — Galina Yakovleva
(74) *Attorney, Agent, or Firm* — Brinks Gilson & Lione

(57) ABSTRACT

The present invention relates to new methods and reagents for coupling molecules by a Click reaction using a heterogeneous catalyst system. Further, the present invention refers to novel devices for carrying out Click reactions.

19 Claims, 9 Drawing Sheets

Figure 1
(a)
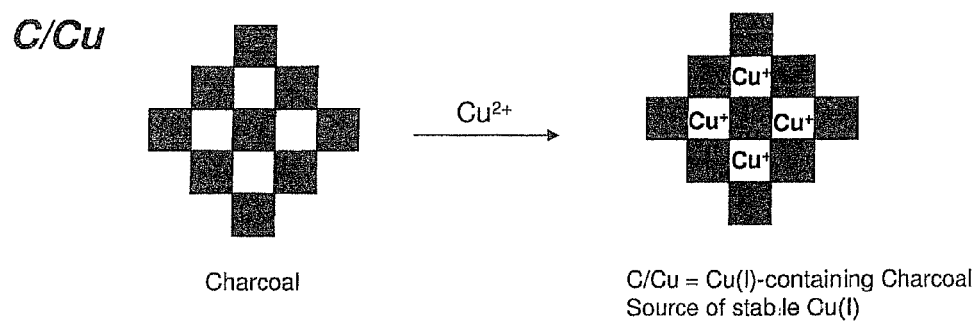
Charcoal
C/Cu = Cu(I)-containing Charcoal
Source of stable Cu(I)
(b)
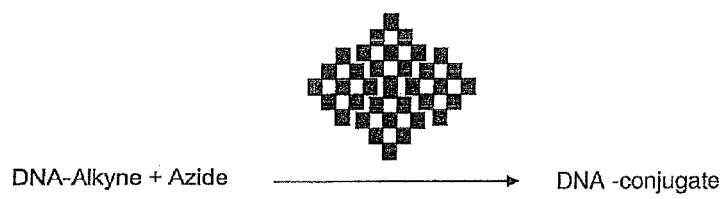
DNA-Alkyne + Azide ⟶ DNA-conjugate

CLICK CHEMISTRY ON HETEROGENEOUS CATALYSTS

This application is a National Stage application of International Application No. PCT/EP2010/054645 filed Apr. 8, 2010, which claims the benefit of U.S. Provisional Application No. 61/167,981, filed Apr. 9, 2009, the entire contents of which are hereby incorporated herein by reference. This application also claims priority under 35 U.S.C. §119 to EP Patent Application No. 09005239.0, filed Apr. 9, 2009, the entire contents of which is hereby incorporated herein by reference.

The present invention relates to new methods and reagents for coupling molecules by a Click reaction using a heterogeneous catalyst system. Further, the present invention refers to novel devices for carrying out Click reactions.

BACKGROUND OF THE INVENTION

In 2001/2002 the groups of Sharpless and Meldal independently defined the concept of "Click chemistry" and the criteria for a transformation to be considered a "Click" reaction [2] and [3]. Since then, the copper catalysed reaction of azides with alkynes to give 1,2,3-triazoles (the 1,3-dipolar Huisgen cycloaddition[1]) has become the most widely used Click reaction. As a result of its mild conditions and high efficiency, this reaction has found a myriad of applications in biology and materials science, such as DNA labelling purposes [16].

One of the limitations of the method when applied to biomolecule labelling concerns the use of Cu(I) as catalyst of the Click reaction. Cu-ions are toxic to bacterial and mammalian cells, thus limiting the use of reaction inside living systems. Furthermore, for DNA, and RNA, improper handling of the catalyst can cause degradation of the oligonucleotides due to Cu-ion catalyzed phosphordiester hydrolysis [17, 18]. Solutions to those problems have been reported and include the in situ Cu(I) generation and/or the use of Cu(I)-stabilizing ligands. The latter is limited to substrates and experimental conditions, which tolerate the presence of organic solvents involved in the Click reaction in order to dissolve the organic ligand (generally a tertiary amine). Molecules such as proteins or long DNA strands eventually precipitate or form insoluble agglomerates upon the addition of even small amounts of organic solvents thus negatively affecting the outcome of the Click reaction.

In any case free Cu(I) ions have a limited life time under ambient conditions, being oxidised to the Click reaction-inactive Cu(II). Therefore, the freshly prepared Cu(I) ligand mixture for the Click reaction needs to be handled carefully and rapidly. Therefore this procedure can only be used in labor-intense manual work, but not in automated process.

According to recent reviews [4], a Click reaction in the presence of copper(II) sulfate (ca. 1%) and sodium ascorbate (ca. 10%) serves to generate catalytically active Cu(I) in situ in an aqueous medium (e.g. $H_2O$/tBuOH) and is typically preferred. Alternative conditions, such as in situ oxidation of Cu(0) or direct introduction of Cu(I) salts (usually CuI or CuBr), have also been used [5]. While both reaction partners have been individually coupled under solid phase conditions, (e.g. on polystyrene) [3, 6], examples of Click chemistry mediated by a source of heterogeneous copper(I) are rare. One report relies on chelation to potentially labile copper by a polystyryl-based benzylic amine [7a]. Only unhindered, low-molecular-weight, and non-basic nitrogen-containing examples were studied therein, without data quantifying losses of copper from the solid support. Other studies are also limited, based on suspensions of unsupported copper clusters [7b].

Lipshutz et al. recently described the virtues of copper-in-charcoal (Cu—C) as a simple, inexpensive, and especially general and efficient heterogeneous catalyst for use in this emerging area [19]. Impregnation of activated wood charcoal (Aldrich, 100 mesh, $53.90/kilo)[8] with a source of Cu(II), e.g. $Cu(NO_3)_2$ in water using an ultrasonic bath was described to lead, after distillation of water and drying, to nanoparticle-sized Cu(I)—C [9]. The Cu(I) is generated from Cu(II) not in an in situ reduction, but via a charcoal-mediated reduction, which allows pre-assembling and storage of the so-generated Cu(I) source for extended time. As both CuO and $Cu_2O$ have been proposed as the species present within a charcoal matrix [10], the presence of Cu(I) suggested that a reducing agent might not be needed. Indeed, the authors have shown that upon mixing benzyl azide with phenylacetylene (1:1) in dioxane at room temperature in the presence of 10 mol % Cu—C, cycloaddition was complete within 10 hours. Filtration and solvent evaporation afforded pure triazole regiospecifically and near-quantitatively [19]. Furthermore, Lipshutz et al. demonstrated the absence of free Cu(I) in solution, corroborating the heterogeneous nature of the Click-reaction event.

In conclusion, Lipshutz et al. reported that highly efficient Click chemistry between organic azides and terminal alkynes can be heterogeneously catalyzed by copper nanoparticles mounted within the pores of activated charcoal [9]. Furthermore, the authors have shown that reactions can be accelerated with stoichiometric $Et_3N$ or by simply increasing the reaction temperature. Under microwave irradiation, triazoles can be formed in minutes at 150° C. Cycloadditions can be carried out in a purely organic medium, in aqueous solvent mixtures, or in pure water. Solubility issues, copper contamination, and modest yields usually associated with the choice of copper salt are completely averted. External ligands known to accelerate Click reactions are not needed. The catalyst appears to be unaffected by exposure to air, suggesting a substantial shelf life. Steric congestion in one or both partners is well tolerated, and product isolation is notably facile, as Lipshutz et al. [19] demonstrated.

The use of Cu/C catalysts for Click reactions with organic molecules in free form is also disclosed in [20] and [21]. None of these documents, however, describes a Click reaction wherein one of the Click partners is immobilized on a solid carrier.

Click reactions involving the use of biomolecules are disclosed in [16], [22], [23] and [24]. These reactions are performed in the presence of a soluble catalyst.

The present invention describes the application of heterogeneous catalysts, particularly Cu(I)—C-catalysts for the labelling of biomolecules such as DNA and many possible easy-to-use devices or methods based on this invention, several of which are shown in this application as proof-of-concept and example.

SUMMARY OF THE INVENTION

The present invention relates to Click reactions carried out on biomolecules in the presence of a heterogeneous catalyst, preferably in an aqueous phase, e.g. for the labelling of biomolecules such as nucleic acids. The present invention paves the way for a new and easy-to-use biomolecule-labelling process and for easy-handling and/or automated biomolecule-labelling protocols.

The Click reaction is hereinafter intended as a reaction between a 1,3-dipolar moiety, particularly an azide, with an unsaturated moiety, particularly an alkyne, catalysed by a heterogeneous catalyst, e.g. a heterogeneous copper (I) or other metal catalyst. Preferably, the Click reaction comprises a (3+2) 1,3-dipolar cycloaddition resulting in a 5-membered heterocyclic moiety, such as 1,2,3-triazole moiety.

A first aspect of the present invention relates to a method of coupling a first molecule to a second molecule by a Click reaction, wherein the first molecule comprises a first Click functional group which is a Click-reactive unsaturated group, and the second molecule comprises a second complementary Click functional group which is a Click-reactive 1,3-dipolar group capable of reacting with the first Click-functional, group by a Click reaction, comprising contacting the first and second molecule in the presence of a heterogeneous catalyst under conditions wherein a Click reaction between the first and second molecule occurs, wherein one of the first and second molecules is a biomolecule.

A further aspect of the present invention relates to a method of coupling a first molecule to a second molecule by a Click reaction, wherein the first molecule comprises a first Click functional group which is a Click-reactive unsaturated group, and the second molecule comprises a second complementary Click functional group which is a Click-reactive 1,3-dipolar group capable of reacting with the first Click-functional group by a Click reaction, comprising contacting the first and second molecule in the presence of a heterogeneous catalyst under conditions wherein a Click reaction between the first and second molecule occurs, wherein one of the first and second molecules is immobilized on a solid carrier, e.g. on the heterogeneous catalyst and/or on a further solid carrier material, e.g. a chromatographic material. In such embodiment, the Click-reaction may be considered a "Click on solid support".

A further aspect of the present invention relates to a device having at least one reaction chamber, wherein the reaction chamber comprises a heterogeneous catalyst for carrying out a Click-reaction and optionally a further solid carrier material, wherein a partner of the Click-reaction may be immobilized on said heterogeneous catalyst and/or on said further solid carrier material, particularly for use in the methods as described above.

Still a further aspect of the present invention refers to a device having at least one reaction chamber, comprising the heterogeneous catalyst for a Click-reaction and optionally one of the partners for the Click-reaction immobilized thereon, preferably a partner comprising a Click-reactive 1,3 dipolar group.

Still a further aspect of the present invention refers to a reagent kit for a Click reaction comprising a device having at least one reaction chamber, wherein the reaction chamber comprises a heterogeneous catalyst for carrying out a Click-reaction and optionally a further solid carrier material, wherein a partner of the Click-reaction may be immobilized on said heterogeneous catalyst and/or on said further solid carrier material, and a first and second molecule, wherein the first molecule comprises a first Click-functional group, which is a Click-reactive unsaturated group, and the second molecule comprises a second complementary Click-functional group which is a Click-reactive 1,3-dipolar group.

Still a further aspect of the present invention relates to the use of the above methods and reagents for producing labelled biomolecules. These labelled biomolecules may be used for detecting an analyte, e.g. a nucleic acid in a sample, particularly involving the use of a compound labelled by a Click-reaction, which forms an association product with the analyte to be detected.

An embodiment of this aspect relates to a method for detecting an analyte in a sample comprising the steps:

(i) providing a device having at least one reaction chamber, wherein the reaction chamber comprises a heterogeneous catalyst for carrying out a Click-reaction and optionally a further solid carrier material, wherein one partner of the Click-reaction may be immobilized on said heterogeneous catalyst and/or on said further solid carrier material, (ii) contacting in said reaction chamber a first molecule which is a first Click partner with a second molecule which is a second Click partner in the presence of the heterogeneous catalyst under conditions wherein a Click reaction between the first and second molecule occurs, wherein the second molecule preferably comprises a reporter group or a reporter precursor group, (iii) if necessary, converting reporter precursor groups to reporter groups, (iv) contacting the coupling product of the first molecule and the second molecule with the sample under conditions which allow detection of the analyte, and (v) qualitatively and/or quantitatively detecting the analyte, preferably via said reporter group.

Preferably, the analyte detection comprises an automated procedure. More preferably the Click-reaction and analyte detection are carried out within a single integrated apparatus.

The present invention allows a highly sensitive detection of an analyte and the design and synthesis of new conjugates connected via a heterogeneous catalysed Click reaction suitable for life science research, molecular diagnostic, pharmaceutical and nanotechnology applications. Preferred applications include, but are not limited to, the detection of genetic variabilities, e.g. single nucleotide polymorphisms (SNPs), pesticide or medicament resistances, tolerances or intolerances, genotyping, e.g. the detection of species or strains of organisms, the detection of genetically modified organisms or strains, or the detection of pathogens or pests, and the diagnosis of diseases, e.g. genetic diseases, allergic diseases, autoimmune diseases or infectious diseases. A further preferred application is the detection of nucleic acids in samples for brand protection, wherein products such agricultural products, food products, or goods of value and/or packaging of these products are encoded with product-specific information, e.g. but not limited to production site, date production, distributor etc., and wherein this information is detected with the methods as described above.

DETAILED DESCRIPTION OF PREFERRED EMBODIMENTS

The present invention provides methods and reagents that allow an easy-to-use and specific labelling of analytes with reporter groups by a Click reaction. Furthermore, the invention provides methods and reagents that allow specific formation of conjugates from two or more partners by single or multiple Click reactions. The Click reaction is effected between a first molecule and a second molecule in the presence of a heterogeneous catalyst. One of these molecules is a Click partner which comprises an unsaturated Click-reactive group, preferably an alkyne group, capable of reacting with a Click-reactive 1,3-dipolar group, preferably an azido group, by a Click reaction. The other molecule is a complementary Click partner which comprises a Click-reactive 1,3-dipolar group, preferably an azido group.

In a preferred embodiment, one of the Click-reaction partners, or more than one partner in case of multiple Click-reactions, may be immobilized, e.g. covalently or non-covalently supported and/or adsorbed on the heterogeneous catalyst and/or a further solid carrier material, resulting in a ready-to-use kit. Furthermore, such kits may be re-usable after a washing step.

Preferred examples of Click-reactive unsaturated groups are dipolarophiles such as alkenes and alkynes and molecules that possess related heteroatom functional groups (such as carbonyls and nitriles). Especially preferred examples of Click-reactive unsaturated groups are alkynes.

Preferred examples of Click-reactive 1,3-dipolar groups are compounds containing one or more heteroatoms which can be described as having at least one mesomeric structure that represents a charged dipole. Preferred are linear 1,3-dipolar groups, e.g. propargyl-allenyl-type dipoles such as

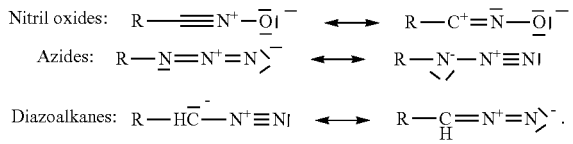

A Click partner comprises a functional group which may react with a complementary Click partner in a cycloaddition reaction wherein a cyclic, e.g. heterocyclic linkage between the Click-functional group and the reaction partner is formed. An especially preferred example of such a Click reaction is a (3+2) cycloaddition between azide and alkyne groups which results in the formation of 1,2,3-triazole rings. Thus, a coupling product may be generated by performing a Click reaction of partners comprising an azide and alkyne group, respectively.

An especially preferred embodiment of the Click reaction comprises a copper catalyzed (3+2) cycloaddition, e.g. between an azide and an alkyne group. The irreversible formation of 1,2,3-triazoles as a result of the azide/alkyne cycloaddition is orthogonal, the required chemical groups are small (incorporation with minimal disruption of the biomolecule's environment) and selective due to the lack of azides and alkynes found in nature.

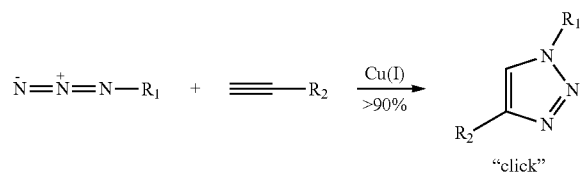

wherein $R_1$ and $R_2$ are first and second molecules.

The method of the present invention encompasses a Click reaction in the presence of a heterogeneous catalyst. The heterogeneous catalyst is preferably a heterogeneous Cu-catalyst, more preferably a heterogeneous Cu(I)-catalyst. It should be noted, however, that other heterogeneous metal catalysts such as Zr, W, Fe, Ru, Co, Rh, Ir, Ni, Pd, Pt, Ag, Au, Zn, Cd, Hg and other metal ions which contribute directly or indirectly to a catalysis of the Click reaction ligation may be used. In a preferred embodiment, the heterogeneous catalyst is a metal-C-catalyst, i.e. a catalyst comprising a carbon-based support such as charcoal having incorporated metal ions therein, e.g. Cu(I)-ions. In an especially preferred embodiment the heterogeneous catalyst is a Cu(I)—C-catalyst, e.g. a Cu(I)-charcoal catalyst which may be prepared as described in [19].

A schematic depiction of a suitable Cu(I)-charcoal catalyst and its manufacture is shown in FIG. 1a. The charcoal is loaded with a source of Cu(II), which is reduced by the charcoal and incorporated therein to provide a source of stable Cu(I). A preferred embodiment of a Click-reaction between a first and a second molecule, i.e. the reaction between a DNA-alkyne and an azide in the presence of the heterogeneous catalyst, is shown in FIG. 1b.

The heterogeneous catalyst may be a particulate catalyst, e.g. a heterogeneous catalyst consisting of particles having a size of from 10 nm to 1000 µm, preferably from 10 µm to 200 µm or from 10 nm to 1000 nm. Alternatively, the catalyst may also be a porous non-particulate catalyst, e.g. a solid matrix having embedded therein catalytically active particles.

In addition, the reaction may be carried out under conditions, wherein one of the reaction partners is immobilized on a solid carrier material, which is able of physical interaction with the reagents and/or products of a Click reaction (nucleic acids or other Click partners). The solid carrier material is preferably a solid carrier material, e.g. a particulate or non-particulate solid material capable of immobilizing a partner of the Click-reaction. In one embodiment, the solid carrier material may be the heterogeneous catalyst, e.g. a Cu(I)—C-catalyst on which e.g. Click-functionalized reporter molecules, e.g. fluorescent or non-fluorescent dyes or biotin, may be adsorbed. In a further embodiment, the solid carrier material is a material different from the heterogeneous catalyst, e.g. a chromatographic material on which a biomolecule such as a nucleic acid, a nucleic acid analog, a protein or a peptide may be immobilized. In these embodiments, the Click-reaction can be carried out under conditions, wherein the first and/or the second reaction partner is immobilized on the solid carrier and the other partner is free in solution.

Examples of suitable chromatographic materials are an ion exchange material, a hydrophilic material or a hydrophobic material. In a preferred embodiment a hydrophilic material, e.g. silica gel, can be used in combination with the heterogeneous catalyst, e.g. Cu(I)/C. In another preferred embodiment a hydrophobic material, e.g. silica C18 or C4 or a ion exchange resin, can be used in combination with the heterogeneous catalyst, e.g. Cu(I)/C. In a still further preferred embodiment, the solid carrier material may be a resin which is used for the solid phase synthesis of biomolecules, e.g. nucleic acids, nucleic acid analogs, proteins or peptides.

Surprisingly, it was found that the Click-reaction between an immobilized reaction partner (e.g. a covalently or non-covalently immobilized reaction partner) and a reaction partner present free in solution may be effectively catalyzed by a heterogeneous catalyst system. This strategy may allow achieving simultaneously the Click reaction and the purification and/or the separation of the product from the impurities and/or from salts eventually present in the reagent solution.

In a preferred embodiment of the invention, the Click-reaction is carried out in a device which comprises at least one reaction chamber, e.g. a pipette tip, a spin column, a reaction chamber on a biochip or in a microtiter plate, etc. The reaction chamber comprises the heterogeneous catalyst and optionally a further solid carrier material as described above for immobilizing a reaction partner. The catalyst and the carrier material may be present in a single reaction chamber, e.g. as a physical mixture of particles or as a heterogeneous solid matrix or in separate compartments of the reaction chamber.

The Click-reaction partners may be passed simultaneously or sequentially into the reaction chamber. If the reaction chamber comprises a solid carrier, it is preferred first to pass the reaction partner to be immobilized into the chamber under conditions, wherein immobilization takes place. In this embodiment, the immobilized reaction partner is preferably a biomolecule, e.g. a nucleic acid or a peptide or polypeptide. Then, the free Click partner, e.g. a Click functional reporter molecule may be passed into the reaction chamber under conditions, wherein a Click-reaction between the immobilized and the free Click partner may be effected.

In a further preferred embodiment, a solid carrier material (i.e. the catalyst and/or optionally the further carrier material) may be pre-impregnated with one of the reaction partners and provided in a dry form. A liquid medium comprising the other reaction partner may then be passed over the solid carrier material, under conditions wherein a Click-reaction between the immobilized and the free Click-partner occurs.

The respective amounts of heterogeneous catalyst and further carrier material can be varied to a large extent. For example, catalyst and further carrier material may be present in ratios of 1:1000 to 1000:1 by weight. After the Click-reaction has been effected, a coupling product is preferably eluted from the solid carrier material, e.g. by changing temperature and/or medium composition (e.g. by changing the amount of salt and/or organic solvents, etc.).

According to the present invention the Click-reaction is preferably carried out in an aqueous medium, i.e. in a liquid medium comprising at least 60% (v/v), preferably at least 75% (v/v), even more preferably at least 90% (v/v) and even more preferably at least 95% (v/v), 98% (v/v) or 99% (v/v) water. Most preferably the aqueous medium is free from organic solvents. In addition to water, the liquid medium may comprise suitable buffer substances or further auxiliary agents, if desired. Alternatively, the reaction may be carried out in an organic or aqueous/organic liquid medium using organic solvents which are compatible with the respective heterogeneous catalyst.

According to the present invention it was found that a heterogeneously catalysed Click reaction may be carried out effectively at ambient temperatures. Generally, the reaction temperature may be varied between about 4 and about 80° C. or higher, particularly between about 10 and about 40° C. Most preferably, the reaction is carried out at a temperature of about 15 to about 25° C.

Further, it was found that the heterogeneously catalysed Click reaction according to the invention proceeds reasonably fast in order to provide convenient and simple protocols for the labelling of biomolecules. For example, the reaction time may be between about 1 min and about 10 min or longer, particularly between about 2 min and about 5 min. In particular cases, longer reaction times may be needed, particularly between 10 min and 4 hours or between 10 min and 8 hours.

The heterogeneously catalysed Click reaction can be accelerated by the presence of amines or other molecules, which interact with the heterogeneous catalyst and/or with the substrates. In a preferred embodiment up to 10% (v/v), more preferably up to 1% (v/v) and most preferably up to 0.1% (v/v) amine is added to the catalyst/reagent mixture. The amine may be a primary, secondary or tertiary amine, which may have an aromatic, heteroaromatic, aliphatic, cycloaliphatic, unsaturated or fully saturated backbone. Preferably, the amine is a tertiary amine such as triethylamine.

Further, the heterogeneously catalysed Click-reaction can be accelerated by different sources of energy, such as sources of microwave or infrared radiation.

Furthermore, it was found that the reaction may proceed in very small volumes, e.g. in reaction volumes occurring in microtiterwells, pipette tips or spin columns. For example, the reaction may proceed in a reaction chamber having a volume may be from about 0.1 to about 1000 µl or more, preferably from about 0.1 µl to about 100 µl, and more preferably from about 0.1 µl to about 10 µl. In an especially preferred embodiment the reaction is carried out in a pipette tip, e.g. in a pipette tip which has provided therein a predetermined amount of heterogeneous catalyst. In a further preferred embodiment the reaction may be carried out in a spin column having incorporated therein a predetermined amount of heterogeneous catalyst. In a different preferred embodiment the reaction can be performed inside a syringe, filled up to 10 ml (for large scale Click reactions), or from 1 to 5 ml, or preferably from 0.1 to 1 ml with the heterogeneous catalyst in a defined volume.

In one embodiment of the invention, the first and/or the second molecules are selected from:
(1) natural and non-natural amino acids and their oligomers and polymers, such as peptides, rotaxane, glycopeptides, proteins, enzymes, antibodies, etc.,
(2) nucleic acids and nucleic acid analogs such as DNA, RNA, LNA, PNA, MeO-RNA, phosphorothioate nucleic acids, etc.,
(3) lipids such as fatty acids and their derivatives, e.g. fatty acid esters, phospholipids, sphingolipids and lipids containing structures such as liposomes, micelles, cell membranes, etc.,
(4) polymers and bio-polymers or their monomers, gels and membranes
(5) viruses, vitamins, hormones, neurotransmitter such as dopamine, adrenaline, serotonin, etc.,
(6) saccharides such as mono-, oligo- and polysaccharides,
(7) macromolecules such as organic and inorganic particles, glass surfaces, silicon materials, silica beads, magnetic beads, metal nanoparticles, metal complexes, metallocenes, dendrimers, glycodendrimers, nanotubes, fullerenes, quantum dots.

Such molecules have already been employed for Click reactions, however, not a combination with a heterogeneous catalyst. An extensive overview can be found in the book "Click Chemistry for Biotechnology and Materials Science" Ed. Joerg Laham, Wiley 2009, the content of which is herein incorporated by reference.

In a preferred embodiment, one of the first and second molecules is a biomolecule, e.g. a molecule selected from nucleosides, nucleotides, amino acids, peptides, saccharides and lipids, including naturally-occurring and modified nucleotides or nucleic acids. More preferably, the biomolecule is selected from nucleic acids, including modified nucleic acids. The biomolecule may be present as free molecule or in an immobilized form, e.g. covalently or non-covalently bound to a solid carrier material as described above.

The other one of the first and second molecules may be a
(i) a reporter molecule,
(ii) an affinity molecule,
(iii) a solid phase,
(iv) a biomolecule, e.g. a protein or a lipid,
(v) a linker or a spacer, which may comprise an aliphatic or cycloaliphatic group, an aromatic or heteroaromatic group, an alkene group, an alkyne group, and/or a polymeric group, e.g. a polyethylene glycol group,
(vi) a pharmaceutical compound or group, a photoactive group, and/or a redox active group, and/or a recognition site.

The reporter molecule may be any molecule which can be detected by known analytical methods. Preferably the reporter molecule is a dye, i.e. a molecule detectable by optical methods. The dye may be a fluorescent, luminescent or otherwise optically detectable dye. The affinity molecule may be any molecule which can specifically from a non-covalent affinity bond to a complementary affinity partner such as biotin or a biotin analogue, which may form an affinity bond with streptavidin or avidin, or a hapten, which may form an affinity bond with an antibody. The solid phase may be any solid phase suitable in analytic methods, e.g. the surface of chips, microwells etc. or particles. The second Click partner may also be any natural occurring or synthetic polymer with a defined or undefined distribution, e.g. a polyethylene glycol, or a drug or a combination of those molecules.

In an especially preferred embodiment, a first molecule, which is a biomolecule, is reacted with at least one second molecule, which is a reporter or affinity molecule or a reactive compound for coupling to a reporter or affinity molecule. The first molecule preferably comprises at least one alkyne group and each second molecule preferably comprises an azide group.

There are substantial advantages for the labelling of biomolecules in an aqueous medium in the presence of a heterogeneous catalyst by a Click reaction. These advantages may be summarized as follows:

1. A heterogeneous catalyst is stable under ambient conditions and does not cause damage of biomolecules, e.g. strand breaks in nucleic acids. Thus, the metal catalyst can be pre-manufactured and stored for long periods. This represents a very important improvement for Click reactions, especially with biomolecules.

2. The reaction may be carried out in the absence of non-water soluble metal ligands, e.g. Cu(I)-ligands.

3. The reaction can be carried out in an aqueous medium, i.e. in the absence of organic solvents such as DMSO and/or t-butanol. These organic solvents are not optimal for longer nucleic acid molecules, i.e. DNA strands of more than 30 nucleotides. Further, these molecules are incompatible with polypeptides or with a work-up of the reaction mixture with HPLC.

4. The reaction time including preparation, carrying out of the reaction and work-up can be largely reduced by using a heterogeneous catalyst.

5. The heterogeneously catalysed Click reaction can be used in automated processes, e.g. in automated labelling processes such as on an automated DNA-synthesizer allowing an extended industrial use of Click-chemistry.

6. Charcoal is normally used for decolouring and purifying reaction mixtures.

Thus, one more advantage of using heterogeneous carbon-based catalysts, e.g. Cu(I)/C catalysts, consists of a one-step reaction-purification. This effect can be increased by the use of a mixture or matrix of Cu(I)/C with, e.g. C18 material, which retains a nucleic acid molecule, e.g. an oligo nucleotide during and after the Click reaction, allowing the washing out of salts and other impurities and allowing the concentration of the sample. The final elution of the product, e.g. a nucleic acid conjugate may be then achieved in presence of an appropriate eluent, e.g acetonitrile/water 1:1, or 8:2 or in different compositions.

7. The reaction may be carried out in the presence of a solid carrier material having immobilzed thereto either the first or the second reaction partner. This allows efficient purification and/or separation of the desired reaction product.

A comparison of a typical prior art Click reaction protocol (FIG. 2) and an inventive Click reaction protocol (FIG. 3) demonstrates the above advantages.

In a further preferred embodiment, one of the reaction partners (e.g. the Click-reactive fluorescent or non-fluorescent dye or a biomolecule such as DNA) can be previously adsorbed directly on a solid carrier, which may be the heterogeneous catalyst (e.g. Cu—C) and/or a further solid carrier material. Thereby a ready-to-use kit is provided, e.g. for biomolecule-labelling, comprising (a) the heterogeneous catalyst and optionally a further solid carrier material, and (b) one of the partners of the Click-reaction, preferably the label, which may be non-covalently immobilized on the catalyst and/or the further solid carrier material. This greatly facilitates the labelling protocol of biomolecules, e.g. oligonucleotides or proteins reducing the hands-on work to simply dispense the biomolecule to be labelled into the reaction chamber comprises a pre-adsorbed solid phase (e.g. Cu—C-fluorescein, in order to obtain Fluorescence-labelled-biomolecule; Cu—C-Biotin; Cu—C-Alexa550, Cu—C-Eterneon, etc.). Such ready-to-use kits are suitable for automated processes as well.

In an especially preferred embodiment, the first molecule comprising a Click-reactive unsaturated group is a biomolecule as described above. This biomolecule preferably comprises a plurality of Click-reactive unsaturated groups which may be the same or different. The second molecule is preferably a reporter molecule as described above, e.g. a fluorescent or non-fluorescent dye.

In an alternative, especially preferred embodiment, the second molecule comprising a Click-reactive 1,3-dipolar group is a biomolecule as described above. This biomolecule may comprise a single Click-reactive 1,3-dipolar group. Preferably, this biomolecule comprises a plurality of Click-reactive 1,3-dipolar groups, which may be the same or different. The second molecule is preferably a reporter molecule as described above, e.g. a fluorescent or non-fluorescent dye.

A further especially preferred embodiment of the present invention comprises a reaction of e.g. an alkyne-modified nucleic acid such as DNA, and an azide-modified reporter group, e.g. a fluorescent or non-fluorescent dye, or alternatively of an azide-modified nucleic acid such as DNA, and an alkyne-modified reporter group, e.g. a fluorescent or non-fluorescent dye, in the presence of a heterogeneous catalyst in water or an aqueous buffer. At the end of the reaction the product may be purified from starting material, if still present in the solution, e.g. by separating the final product from starting material, e.g. by size-exclusion and/or from the heterogeneous catalyst, e.g. by filtration. The product is obtained in an aqueous solution and can be analyzed or used as such after the reaction.

The filtration of Cu/C from the sample can be carried out before, during and/or after the separation of other components from the reaction mixture (e.g. dyes, nucleosides, small molecules and so on). Examples of suitable filtration/purification systems are silica-gel membranes (e.g. Jena Bioscience) to purify DNA fragments larger than 100 bp, centrifugal filter units (e.g. from Jena Bioscience) to remove unincorporated nucleotides, QIAquick PCR Purification Kit (from QIAGEN), Microcon® Centrifugal Filter Devices (from Millipore), Amicon® Ultra-0.5 and Ultra-15 Centrifugal Filter Devices (from Millipore), Ultrafree®-MC and -CL Centrifugal Filter Devices (from Millipore), Acrodisc® 13 mm and 25 mm Syringe Filters (from PALL Science) with 0.2 and 0.45 µm pore size, Costar® Spin-X® Centrifuge Tube Filters with cellulose acetate or nylon membranes, e.g. with 0.22 or 0.45 µm membrane pore sizes, Vectaspin Micro, Anopore™ from Whatman®), Nanosep MF Devices, Sample Reservoir filters, e.g. 13 mm Syringe Filter, 0.2 µm with PTFE, Nylon or Polypropylene Membranes for sample preparation and small volume chemical filtration (from VWR), EconoSpin™ All-in-1 Mini Spin Columns and suitable receiver tubes, Filterplate 96-wells, 1 ml, GF/FF, GF/N and GF/B Filters, RC/5, 10-Ultrafiltration-Microplate, 5 and 10 kD, 96-wells, RC/30 and 100 Ultrafiltration-Microplate, 30 and 100 kD, 96-wells, and AcroPrep 96 and 384 Multi-Well Filter Plates (from PALL).

The present invention also comprises the detection of an analyte. The detection may be a qualitative detection, e.g. the determination of the presence or absence of an analyte, e.g. a specific nucleic acid sequence in the sample to be analysed. The invention, however, also allows quantitative detection of an analyte, e.g. a nucleic acid sequence, in the sample to be analysed. Qualitative and/or quantitative detection may comprise the determination of reporter groups according to methods known in the art.

The analyte to be detected is preferably selected from analytes present in a biological or environmental sample such as biomolecules, drugs or toxic compounds. Examples of biomolecules include nucleic acids, peptides, polypeptides, saccharides, lipids, steroids etc. For example, the analyte may be selected from nucleic acids and nucleoside-, nucleotide- or nucleic acid-binding molecules, e.g. nucleoside-, nucleotide- or nucleic acid-binding proteins. More preferably, the analyte is a nucleic acid, e.g. any type of nucleic acid which can be detected according to known techniques, particularly hybridization techniques. For example, nucleic acid analytes may be selected from DNA, e.g. double-stranded or single-stranded DNA, RNA, or DNA-RNA hybrids. Particular examples of nucleic acid analytes are genomic DNA, mRNA or products derived therefrom, e.g. cDNA.

The method of the invention can be carried out according to any known test format which is suitable for the detection of analytes, particularly nucleic acid analytes in a sample. For example, the method may involve the detection of analytes immobilized on solid surfaces such as membranes, e.g. in Western, Southern or Northern blots, chips, arrays or particles such as beads. Further, the detection can be carried out in gels, e.g. after electrophoretic separation of the sample in gels, e.g. agarose or polyacrylamide gels, chromatographic procedures and/or by mass spectroscopic procedures. The method may involve the detection of single analytes or the parallel detection of a plurality of analytes, e.g. in a chip or microarray format.

The sample may be any sample which may contain the analyte to be detected. For example, the sample may be a biological sample, such as an agricultural sample, e.g. a sample comprising plant material and/or material associated with the site where plants grow, plant materials are stored or processed. On the other hand, the sample may also be a clinical sample, such as a tissue sample or a body fluid sample such as blood, serum, plasma, etc., particularly of human origin. Further types of samples include, but are not limited to, environmental samples, soil samples, food samples, forensic samples or samples from valuable goods which are tested for brand protection.

Due to its high sensitivity, the method of the present invention is suitable for detecting analytes directly without amplification. For example, the detection of an analyte, e.g. a gene, in a biological sample, might be performed by a combination of Southern blotting and the inventive method. It should be noted, however, that the method of the present invention also allows the detection of nucleic acids combined with an amplification step, which may be carried out according to known protocols such as PCR or modifications thereof, such as asymmetric PCR, real-time PCR, reverse transcription PCR, etc., or other amplification protocols such as LCR.

In a preferred embodiment of the invention, a sequence-specific detection of the analyte is carried out, wherein for example a nucleic acid having a specific sequence is distinguished from other nucleic acid sequences in the sample or a polypeptide capable of binding a specific nucleic acid sequence is distinguished from other polypeptides in the sample. Such a sequence-specific detection preferably comprises a sequence-specific hybridization reaction by which the nucleic acid sequence to be detected is associated with a compound carrying a marker group or a marker precursor group. It should be noted, however, that the present invention also allows sequence-unspecific detection of nucleic acids, e.g. detection of any nucleic acids present in a sample.

In order to identify the analyte to be detected, the sample may be contacted with a detection reagent, which is a Click partner, i.e. the first or second molecule as described above, under conditions, wherein an association product with the analyte, e.g. a nucleic acid, is formed. In this embodiment, a Click-reaction may be carried out in the presence of the analyte, i.e. on the formed association product.

In a different embodiment, the first and the second molecules are reacted by a Click-reaction resulting in a labelled detection reagent, which is subsequently contacted with the analyte to be detected. The Click-reaction and analyte may be carried out by an automated procedure, preferably in a single integrated apparatus.

The first molecule may comprise a single Click-functional group or a plurality of functional groups. For example, a molecule may be coupled to a dendrimeric moiety comprising a plurality, e.g. 2, 3, 4, 5, 6, 7, 8 or more Click functional groups as indicated above. Dendrimeric moieties may be synthesized by known techniques. The Click functional groups on the first molecule may be the same or different, e.g. a combination of unprotected alkyne groups and one or several types of protected alkyne groups as described in WO2008/052775, the content of which is herein incorporated by reference. In case the first molecule comprises unprotected and protected Click functional groups, a sequential reaction with several types of different second molecules may take place.

The Click-functional group is attached to a molecule which is capable of forming an association product with the analyte. The molecule may be a nucleosidic or nucleotidic compound, e.g. a nucleoside or nucleoside analogue or a nucleotide or nucleotide analogue or an oligomer or polymer, e.g. a nucleic acid or nucleic acid analogue. A nucleosidic or nucleotidic compound is a nucleoside or nucleotide analogue or a nucleotide or nucleotide analogue capable of being incorporated into nucleic acids or nucleic acid analogues, e.g. by chemical or enzymatic methods. The resulting nucleic acid or nucleic analogue should be capable of forming association products, e.g. nucleic acid hybrids, with the analyte. Preferably, the compound comprises a base moiety, e.g. a nucleobase or another heterocyclic base moiety capable of forming base pairs with a nucleobase, and a backbone moiety, e.g. comprising a sugar moiety and optionally a phosphate moiety in nucleosides or nucleotides or a different backbone moiety in nucleoside or nucleotide analogues.

Preferred examples of functional nucleosidic compounds, wherein the nucleobase is 7-dN-G, C, 7-dN-A or T.

Preferably, the Click-functional group is attached to a base moiety, e.g. to a nucleobase. The Click-functional group, however, may also be attached to a backbone moiety, e.g. a sugar group, a phosphate group or, in the case of nucleoside or nucleotide analogues, a modified sugar group, a modified phosphate group or peptide backbone moiety, etc. Preferably, the functional group is covalently attached to the compound via a direct bond or via a spacer. If the attachment is effected via a spacer, the spacer may comprise an aliphatic or cycloaliphatic group, an aromatic or heteroaromatic group, an alkene group and/or an alkyne group and/or a polyethylene group.

In functionalized nucleosides, nucleotides and nucleic acids a Click group is preferably attached to a nucleobase which may be selected from naturally occurring and non-naturally occurring purine and pyrimidine bases. Preferably, the nucleobases are selected from cytidine, uracil, thymine, adenine, guanine, 7-deazaadenine, 7-deazaguanine, inosine and xanthine. The functional group is preferably attached to position 5 or 6, more preferably to position 5, of a pyrimidine nucleobase or to position 7 or 8, more preferably to position 7 of a purine nucleobase, particularly if an enzymatic incorporation into a nucleic acid is desired.

The Click-functional groups, i.e. the unsaturated group and the 1,3-dipolar group are covalently attached to the first or second molecule, respectively. One or both groups may be attached to the respective molecule via a linker. Preferably, at least the 1,3-dipolar group is attached for its molecule via a linker. A linker-containing group may be attached to its molecule via a direct bond or a linker having a chain length up to 20 atoms. The linker may have a chain length from 1-20 or more atoms and be flexible, e.g. an alkylene-based linker, optionally containing heteroatoms such as O, S, and/or N or at least partially rigid, e.g. a linker which comprises at least one rigid group selected from alkene groups, alkyne groups, cyclic groups, particularly aromatic or heteroaromatic groups, but also cycloaliphatic groups and combinations thereof.

The first or second molecule and/or the coupling product thereof may be capable of forming an association product with the analyte to be detected.

For example, the first or second molecule may be a nucleotide or nucleic acids including modified nucleotides or nucleic acids. The term "nucleotide" according to the present invention particularly relates to ribonucleotides, 2'-deoxyribonucleotides or 2',3'-dideoxyribonucleotides. Nucleotide analogues may be selected from sugar- or backbone modified nucleotides, particularly of nucleotide analogs which can be enzymatically incorporated into nucleic acids. In preferred sugar-modified nucleotides the 2'-OH or H-group of the ribose sugar is replaced by a group selected from OR, R, halo, SH, SR, $NH_2$, NHR, $NR_2$ or CN, wherein R is $C_1$-$C_6$ alkyl, alkenyl or alkynyl and halo is F, Cl, Br or I. The ribose itself can be replaced by other carbocyclic or heterocyclic 5- or 6-membered groups such as a cyclopentane or a cyclohexene group. In preferred backbone modified nucleotides the phospho(tri)ester group may be replaced by a modified group, e.g. by a phosphorothioate group or a H-phosphonate group. Further preferred nucleotide analogues include building blocks for the synthesis of nucleic acid analogs such as morpholino nucleic acids, peptide nucleic acids, locked nucleic acids or phosphorothioates.

Click- or functionalized nucleic acids may be oligonucleotides, e.g. nucleic acids having a length of up to 30 nucleotide (or nucleotide analogue) building blocks or polynucleotides having a length or more than 30 nucleotide (or nucleotide analogue) building blocks. Preferably, the nucleic acids and nucleic analogues are capable of specific binding to an analyte, e.g. capable of hybridizing with a nucleic acid analyte under assay conditions. The minimum length is preferably 12 and more preferably 14 nucleotide (or nucleotide analogue) building blocks.

Functionalized nucleic acid or nucleic acid analogue building blocks may be incorporated into nucleic acids by standard techniques for chemical synthesis and/or by enzymatic incorporation as described in WO2006/117161, the content of which is herein incorporated by reference. The method of the present invention provides various embodiments of analyte detection. Methods for detecting nucleic acids are e.g. described in WO2006/117161, the content of which is herein incorporated by reference.

In a still further embodiment, the method of the present invention may be employed for the in vivo labelling of living cells, e.g. eukaryotic cells including mammalian or human cells, or prokaryotic cells. Such methods are e.g. described in WO 2007/50811 and WO 2007/120192, the content of which is herein incorporated by reference. In this embodiment, the reaction may be carried out in a reaction chamber adapted for receiving and/or maintaining living cells.

Methods for detecting other analytes such as polypeptides, carbohydrates or lipids, drugs or toxic substances may be carried out according to basically known methods, however, involving the use of a reagent comprising a polyethylene glycol Click-functional group, e.g. a polyethylene glycol-azido group, or the coupling product of such a reagent with a complementary Click partner as described above in detail.

For example, the detection method of the invention may be carried out by any known detection protocols, e.g. involving the use of solid supports. For example, a solid support, e.g. a chip or array or a particulate material such as a bead may be provided to which a capture reagent is bound capable of binding, e.g. hybridizing to the analyte to be detected. The solid phase bound analyte may be detected by using which bind analyte and subsequent detection of the bound reagent. This method is particularly suitable for the diagnostic applications in the agricultural and clinical field, e.g. for the detection of analytes, e.g. DNA and/or mRNA from plants, e.g. genetically modified plants, DNA from pathogens or plant pests etc.

The detection of the marker groups in reporter molecules may be carried out according to known methods. For example, metal depositions may be determined qualitatively and/or quantitatively by optical methods and/or electrical methods. Fluorescent marker groups may be determined qualitatively and/or quantitatively by known fluorescent measurement methods, e.g. excitation via a suitable light source such as a laser and detecting the emitted fluorescent light.

In a preferred embodiment, the methods and the reagent kits of the present invention are used for agricultural applications. For example, the invention is suitable for the detection of nucleic acids from plants, plant pathogens or plant pests such as viruses, bacteria, fungi or insects. Further, the invention is suitable for detecting genetic variabilities, e.g. SNPs in plants or plant parts, plant pathogens or plant pests such as insects.

A further application is a detection or monitoring of herbicide, fungicide or pesticide resistances, tolerances or intolerances, e.g. resistances, tolerances or intolerances in fungi, insects or plants in organisms or populations of organisms. The invention is also suitable for rapid genotyping, e.g. for the rapid detection and/or differentiation of species or strains of fungi, insects, or plants. Further, detection and/or differentiation of genetically modified organisms for strains, e.g. organisms or strains of fungi, insects or plants is possible.

Further, the invention is suitable for medical, diagnostic and forensic applications, e.g. in human or veterinary medicine, e.g. for the detection of nucleic acids from pathogens, e.g. human pathogens or pathogens of livestock or pet animals.

Further preferred applications include the detection of genetic variabilities, e.g. SNPs in humans or the detection of medicament resistances, tolerances or intolerances or allergies. Further, the invention is suitable for genotyping, particularly genotyping of humans in order to determine mutations associated with predisposition or enhanced risk of disorders, allergies and intolerances. The invention may also be used for the detection of genetically modified organisms or strains, organisms or strains of bacteria or viruses but also genetically modified life stock animals etc. The invention is particularly suitable for the rapid diagnosis of diseases, e.g. genetic diseases, allergic diseases, autoimmune diseases or infectious diseases.

Furthermore, the invention is suitable for detecting the function and/or expression of genes, e.g. for research purposes.

Still a further embodiment is the use of the method for brand protection, e.g. for detecting specific information encoded in products such as valuable goods like plant protection products, pharmaceuticals, cosmetics and fine chemicals (e.g. vitamins and amino acids) and beverage products, fuel products, e.g. gasoline and diesel, consumer electronic appliances can be marked. Further, packaging of these and other products can be marked. The information is encoded by nucleic acids or nucleic acid analogues which have been incorporated into the product and/or into the packaging of a product. The information may relate to the identity of the manufacturer, to production sites, date of production and/or distributor. By means of the present invention, rapid detection of product-specific data can be carried out. A sample may be prepared from an aliquot of the product which is then contacted with one or several sequence-specific functionalized hybridization probes capable of detecting the presence of nucleic acid-encoded information in the sample.

The invention is also suitable for the field of nutrients. For example, in the feed area, animal nutrients, e.g. corn, are supplemented with a greater quantity of preservatives such as propionic acid. By applying the method of the invention, the addition of preservatives can be reduced. Further, genomic analysis with the method of the invention allows the prediction of an individual's capability to utilize specific nutrients (nutrigenomics).

Still a further preferred embodiment refers to the field of epigenetics. This embodiment particularly refers to an analysis of DNA, e.g. genomic DNA with regard to methylation of cytosine bases. In this embodiment, the DNA may be treated with a cytosine-specific reagent, e.g. hydrazine and/or hydroxylamine. By means of the treatment, a selective reaction of either cytosine or methylcytosine residues occurs. For example, treatment with hydroxylamine leads to a selective modification of cytosine residues. Preferably, the reagent is added in a sub-stoichiometric amount in order to obtain a partial modification of e.g. cytosine residues. Subsequently, the treated DNA is analysed, e.g. by a primer extension reaction using at least one modified nucleic acid building block as indicated above, e.g. a dU and/or dC base. Preferably a Click-modified base, e.g. an alkyne-modified base is used. The primer extension reaction gives a characteristic sequencing ladder resulting from interruptions of the reaction on the modified dC or 5-methyl-dC bases.

The method and reagents of the invention involving the use of a heterogeneously catalyzed Click reaction allow application in several specific embodiments. One embodiment encompasses a direct labelling of biomolecules, e.g. oligonucleotides or peptides on a synthesizer, e.g. an oligo-synthesizer, for an automated biomolecule, e.g. DNA/RNA synthesis. In this embodiment, the Click-reaction or at least one step of a Click-reaction may be carried out when the biomolecule, e.g. the oligonucleotide or peptide is covalently bound to the solid phase. Optionally, further Click-reactions with different Click-partners may be carried out after cleaving the biomolecule from the carrier material. A further embodiment encompasses the labelling of genes inside and outside of cells in vitro and/or in vivo. Still a further embodiment encompasses the labelling of molecules in a nucleic acid amplification format, e.g. in a PCR-format. Further, solid surfaces may be labelled using heterogeneous catalysts as well. Other preferred embodiments include the labelling of biomolecules in a device, e.g. a pipette tip or spin column, partially or entirely filled with the heterogeneous catalyst, and optionally a solid carrier material as described above, including micro-flow systems and HPLC-like applications.

DESCRIPTION OF FIGURES

FIG. 1 is (a) a schematic depiction of a Cu(I) charcoal catalyst and its manufacture and (b) a schematic depiction of a reaction between a first and a second Click-functionalised molecule in the presence of a heterogeneous catalyst.

EXAMPLE 1

ClickTips

A ClickTip is a pipette tip (e.g., 10 µL, 100 µL or 1000 µL) with an approximately defined volume (e.g., 0.2-0.6 µL or higher) bed of heterogeneous catalyst such as Cu(I), supported on a solid porous support, e.g. on charcoal preferably fixed at its end such that there is no dead volume optionally in presence of a chromatographic material such as silica gel and/or C18 and/or C4 and/or a ion exchange resin and/or any other material able to retain one or more of the Click reaction components. Other heterogeneous materials, which catalyse or promote the Click reaction or another covalent bond formation can be used in analogous devices. On the catalyst or on the chromatographic material one of the Click-reaction partners, e.g. a label for a biomolecule, may be provided in an adsorbed form.

Figure 2:
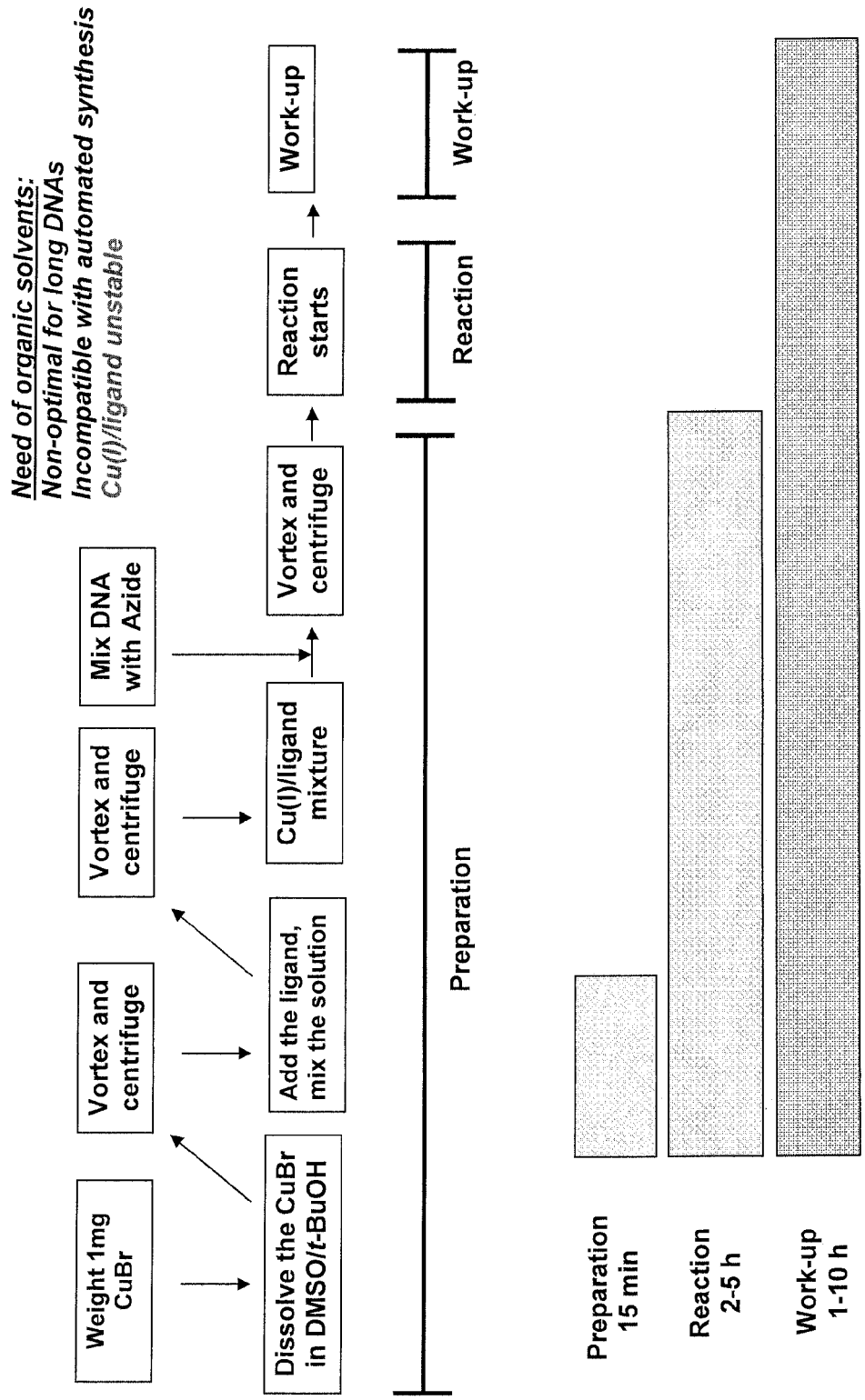
FIG. 2 is a schematic depiction of a prior art Click reaction protocol for DNA-labelling.
Figure 3:
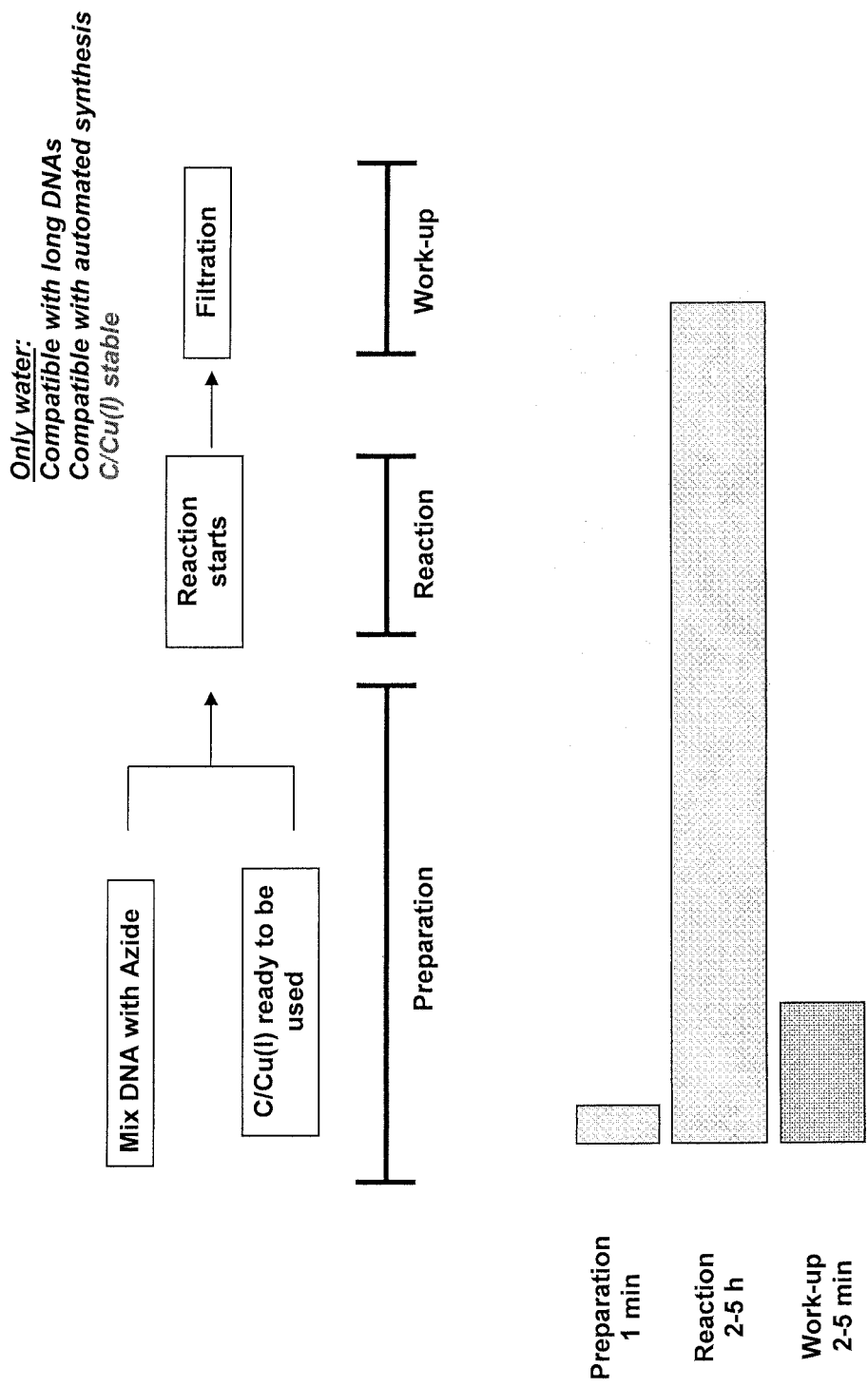
FIG. 3 is a schematic depiction of an inventive Click reaction protocol for nucleic acid labelling using a Cu/C catalyst system.
Figure 4:
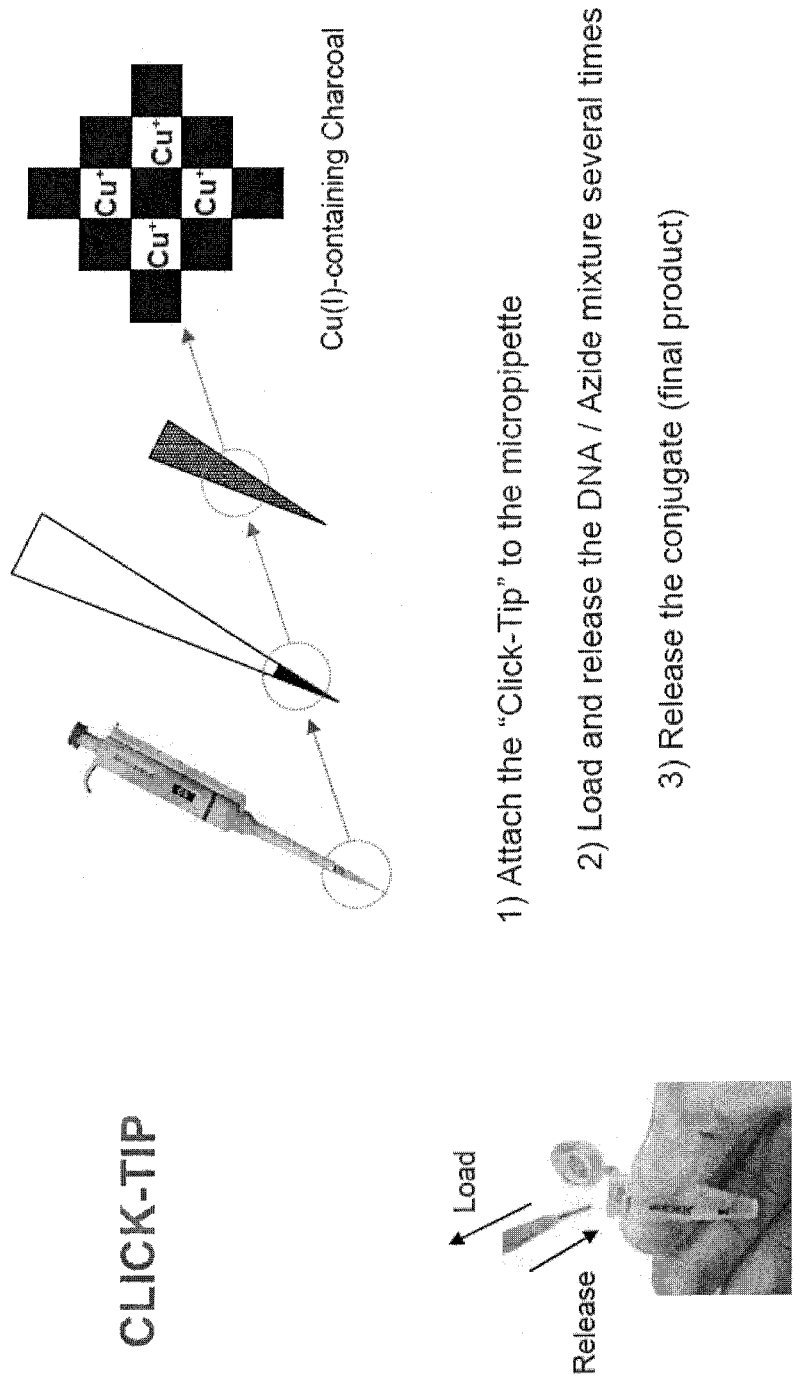
FIG. 4 is a schematic depiction of a Click reaction involving the use of a pipette tip comprising a heterogeneous catalyst system.

The ClickTip pipette tip is simple and easy to use. The tip may be placed on a suitable aspirator, e.g. a single- or multi-channel pipettor, a standard 22-gauge blunt-end HPLC needle, or a compatible automated liquid handling/sample preparation station. For sample processing, the Click-reactive molecules, e.g. DNA-alkyne and label-azide, may be aspirated and dispensed through the support one or several times. The Click reaction occurs during this process on the tip itself (FIG. 4). The newly-formed Click product, e.g. a DNA/label conjugate is finally released and the ClickTip is eventually washed with fresh medium (i.e. water). For applications requiring smaller reaction volumes (e.g., <1 μL), a microbead format containing a smaller volume of support (e.g., 0.2 μL) can be prepared. Large reaction set-ups are possible using larger tips (e.g., 100 μL or 1000 μL). In another preferred embodiment the heterogeneous catalyst is directly combined with a chromatographic material, e.g. C18 or C4 or ion exchange resin in order to afford one-step reaction/purification assays.

EXAMPLE 2

ClickSpins

Figure 5:
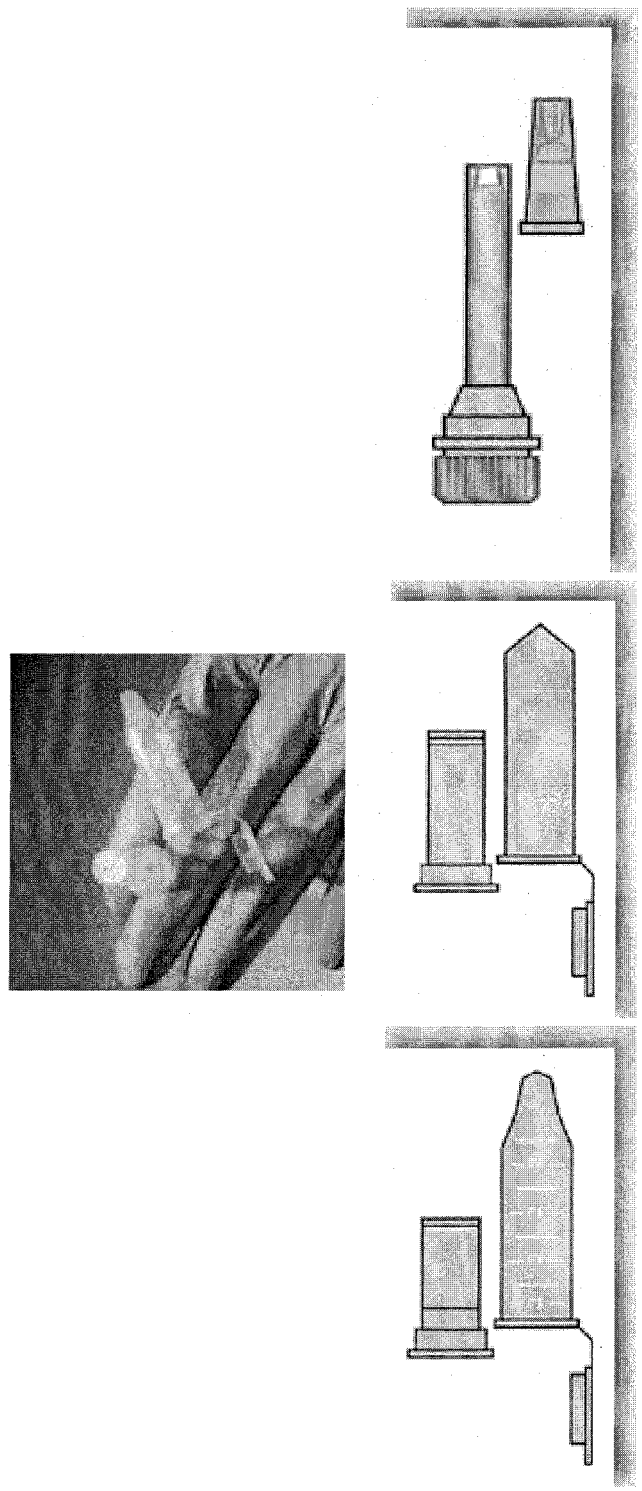
FIG. 5 shows typical examples of spin columns suitable for use in the present invention.

Click-Spins are ready-to-use, microcentrifuge compatible columns for performing a Click reaction and subsequent separation/purification. They consist of two separate parts: a column and a vial (FIG. 5).

Figure 6:
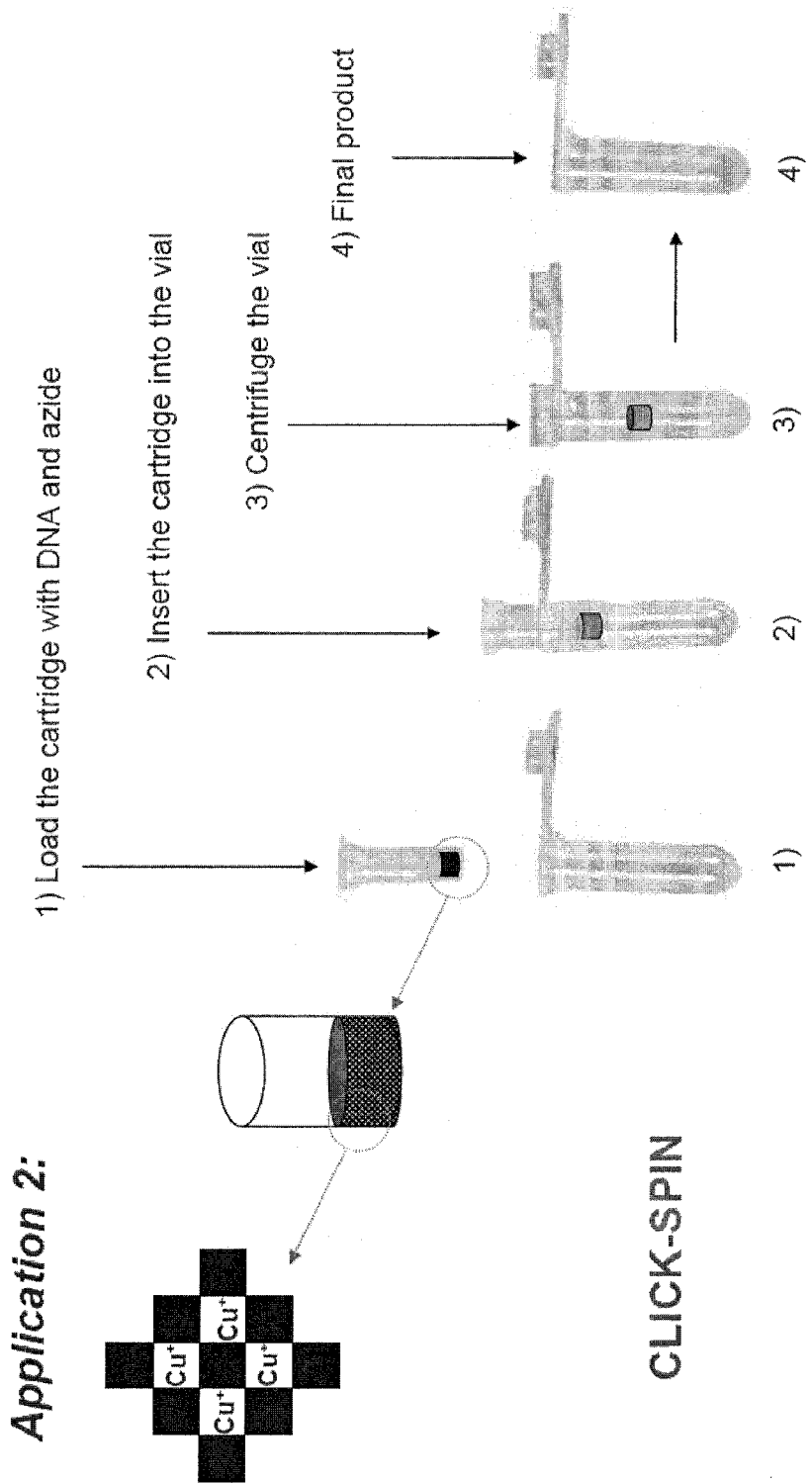
FIG. 6 is a schematic depiction of a Click reaction carried out in a spin column.

The heterogeneous catalyst, e.g. a Cu(I)/charcoal catalyst for the Click reaction can be introduced into the column and fixed therein on a frit, e.g. for size exclusion or for particulate filtration or ion exchange. The Click reaction occurs on the filled column e.g. via standard shaking (with e.g. a Thermomixer) or directly during a centrifugation step (for reactions which proceed fast). The separation/purification step is achieved through centrifugation: the solid support (e.g. the catalyst) is retained on the column (on the filter or on the size exclusion material) and the product, e.g. the conjugated DNA/dye is eluted into the vial. When a size exclusion support is used, the separation step can include the purification of the product from eventually unreacted substrate (FIG. 6). In another preferred embodiment the heterogeneous catalyst is directly combined with a chromatographic material, e.g. C18 or C4 or ion exchange resin in order to afford one-step reaction/purification assays.

EXAMPLE 3

Click Chemistry with Solid Phase Immobilized Molecules

In a further embodiment of the invention, one of the Click partners may be immobilized on the heterogeneous catalyst and/or a further solid material, e.g. a chromatographic material as described in Examples 1 and 2.

Figure 7:
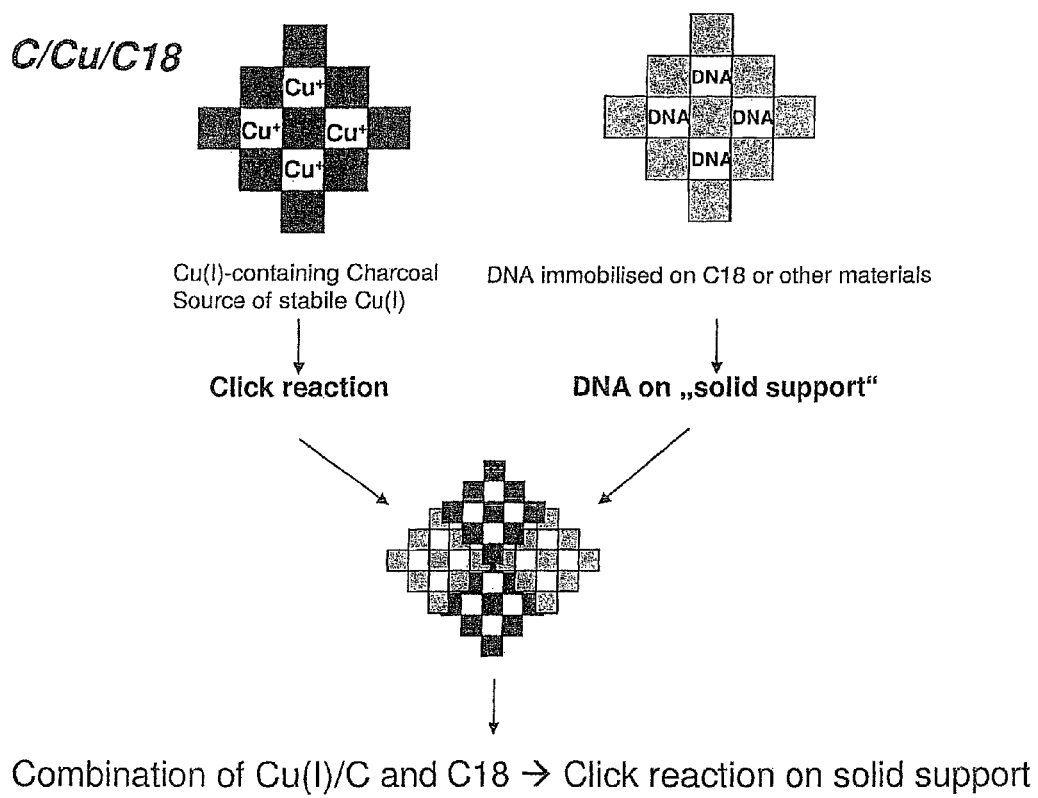
FIG. 7 is a schematic depiction of a Click-reaction carried out with an immobilized biomolecule such as DNA.

In FIG. 7 an embodiment is described wherein the catalyst is combined with a solid carrier, e.g. a DNA immobilizing chromatographic material, e.g. a hydrophobic C18 or C4 resin or an ion exchange resin.

Figure 8:
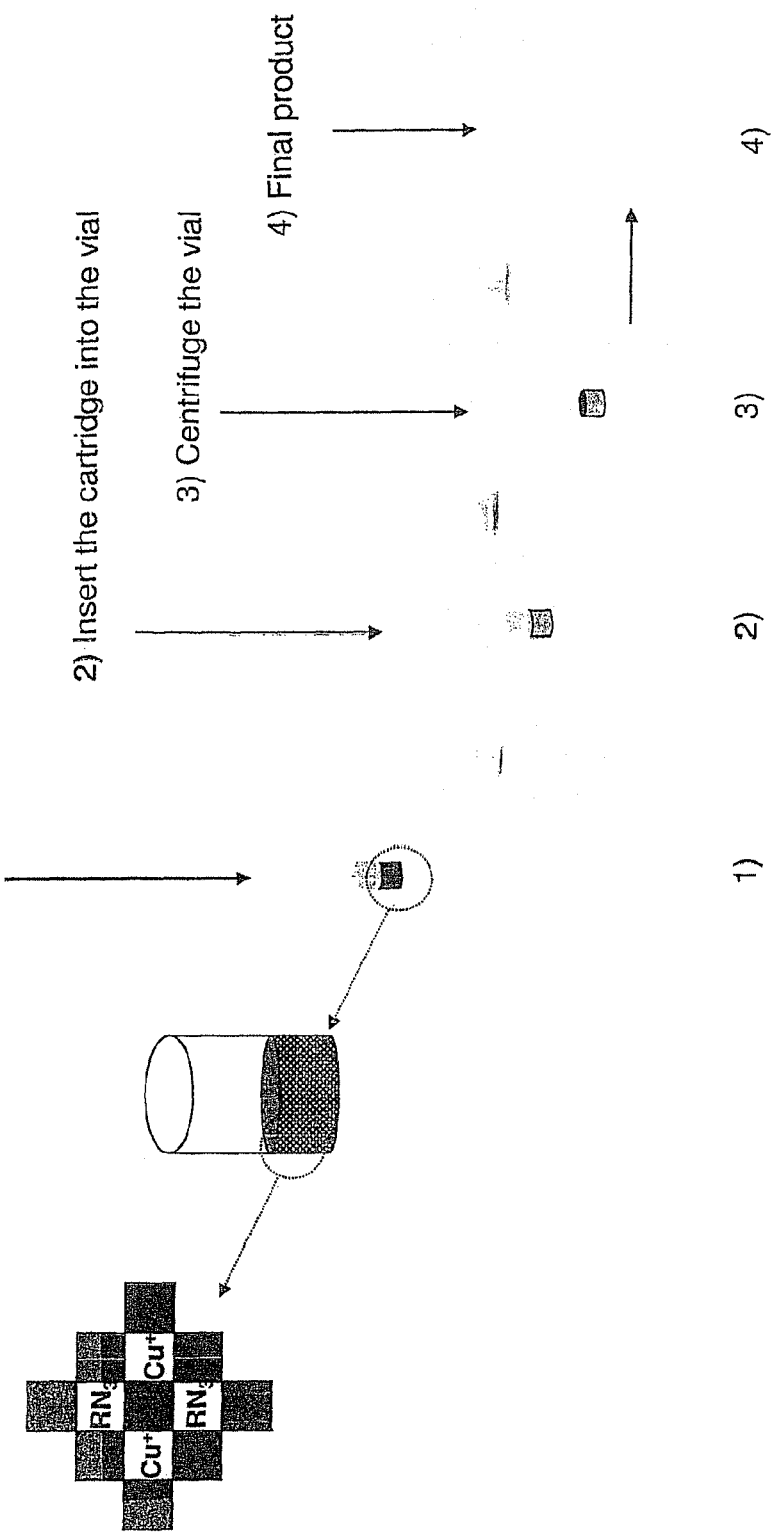
FIG. 8 is a schematic depiction of a Click-reaction carried out with an immobilized reporter molecule such as a label-azide molecule.

The combination of heterogeneous catalyst (e.g. Cu(I) charcoal) and chromatographic material (e.g. C18) allows a Click-reaction on a solid support. This embodiment is schematically described in FIG. 8.

In a still further embodiment, one of the reaction partners, e.g. an azide functionalized reporter molecule ($RN_3$) is immobilized on the heterogeneous catalyst (e.g. C/Cu) before loading the catalyst into a suitable cartridge, e.g. a ClickTip or Click-Spin cartridge as described above. For this purpose the appropriate amount of the functionalized reaction partner in a suitable solvent may be contacted with the catalyst and the solvent may be evaporated. The thus resulting pre-impregnated cartridge is ready to react with a biomolecule, e.g. an alkyne-functionalized biomolecule such as DNA.

For example, the reporter molecule may be selected from fluorescence dyes such as FAM, Cy3, Atto, Eterneon, etc. from other labelling groups, such as biotin.

The heterogeneous catalyst may be combined with a further solid material, e.g. a chromatographic material, such as C18 as described above.

EXAMPLE 4

Click Reaction Protocol for DNA Labelling Using a Heterogenous Catalyst System Molecules comprising alkyne groups (e.g. DNA) and azide-modified reporter groups (e.g. dyes) are mixed and contacted with a heterogeneous catalyst, e.g. a Cu(I)—C catalyst in a suitable device, e.g. a Click-Tip or Click-Spin as described in Examples 1 and 2. The time for this preparation step is up to 1 minute. The Click reaction in the device takes place for preferably 2-5 min, though longer reaction times may be considered. Finally, the reaction product may be worked up, e.g. by filtration which may take up 1 min.

Figure 9:
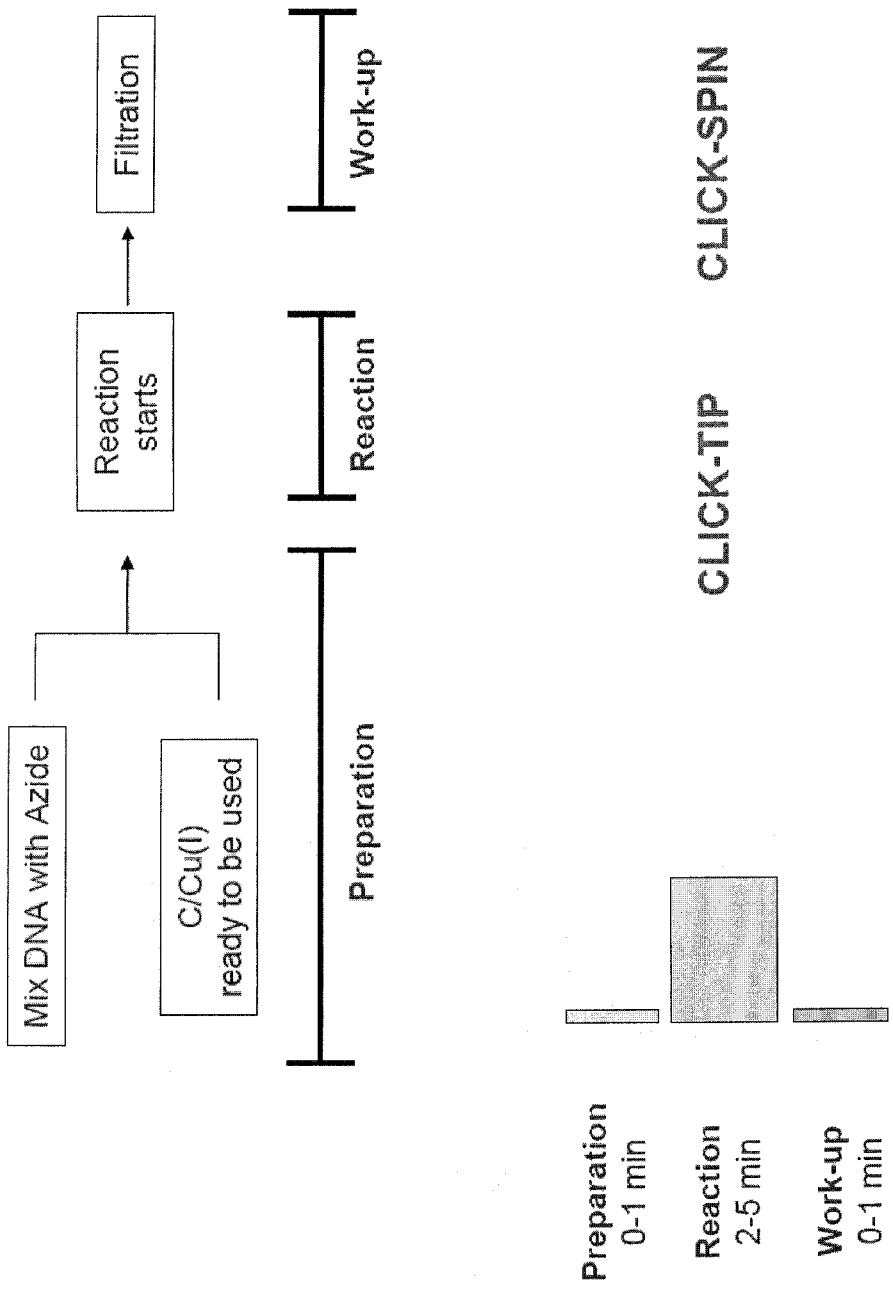
FIG. 9 is a preferred embodiment of a Click reaction protocol for DNA labelling using a heterogenous Cu(I)—C-catalyst and pipette tips (Click Tips) or spin columns (Click Spin).

A schematic depiction of the protocol is shown in FIG. 9.

EXAMPLE 5

Click Reactions in the Presence of a Heterogenous Catalyst 5.1 Preparation of a Cu/C Catalyst Darco KB activated carbon (15.0 g, 100 mesh, 25% $H_2O$ content) was added to a 300-mL round-bottom flask containing a stir bar. A solution of $Cu(NO_3)_2 \cdot 3H_2O$ (Acros Organics, 3.334 g, 13.80 mmol) in deionized $H_2O$ (100 mL) was added to activated carbon, and additional deionized $H_2O$ (125 mL) was added to wash down the sides of the flask. The flask was purged under argon and stirred vigorously for 30 min. Then, the flask was submerged in an ultrasonic bath under a positive argon flow for 1 hour, subsequently attached to an argon-purged distillation setup and placed in a preheated 175-180° C. sand bath with stirring plate. As the distillation ended, the flask temperature began to rise and was held below 210° C. for an additional 15 min. Upon cooling to room temperature, toluene (75 mL) was added to wash down the sides of the flask. The flask was again placed into a hot sand bath until the toluene/$H_2O$ azeotrope had distilled. Once the distillation was finished, the azeotropic distillation was repeated a second time. Upon cooling to room temperature, the black solid was washed with toluene (2×50 mL) under argon into a predried 150-mL coarse-fritted funnel (in vacuo). The fritted funnel was turned upside down under vacuum for 5 h until the Cu/C fell from the frit into the collection flask. The collection flask was then heated in vacuo in a 110-115° C. sand bath for 18 h to further dry the catalyst. The impregnated charcoal (ca. 13 grams) was transferred to and stored in an amber vial. ICP-EAS analysis of the catalyst suggested a loading of 1.01 mmol Cu/g catalyst, or 6.4 wt. % Cu.

The thus prepared Cu/C catalyst has a limited shelf-life of approximately 12 months and >18 months if it stored closed under inert atmosphere.

Preparation of Cu/C in Ethylene Glycol (EG):
120 mg Cu/C was added to 500 μl EG. The mixture was vortexed and centrifuged.

Preparation of Cu/C in Polyethylene Glycol (PEG):
120 mg Cu/C was added to 500 μl PEG. The mixture was vortexed and centrifuged.

5.2 Preparation of Oligonucleotides

Oligonucleotides containing a group Z=C8dC(X), wherein X is defined further below, were prepared according to standard methods.

```
Oligo 1:  22-mer
                                 (SEQ ID NO: 1)
5'-CGCGTATCGCTATCGCTATGGZ-3'

Oligo 2:  5-mer
                                 (SEQ ID NO: 2)
5'-ZCTAG-3'

Oligo 3:  33-mer
                                 (SEQ ID NO: 3)
5'-ZAAAT[C][T]AGAGAATCCCAGAATGCGAAACTCAG- Phosphate-3'
```
[C] and [T] denote modified (LNA) nucleotides 5.3 Definitions of Recovery and Conversion "Recovery" in this text is considered as the percentage of oligonucleotide in nmol obtained after the precipitation step.

"Conversion" in this text is considered the MALDI percentage of product formed in the reaction.

5.4 Sample Preparation for MALDI Measurement

After a reaction, samples were desalted and 0.4 µl of each sample were spotted on a MALDI target together with 0.4 µl of a HPA-C matrix (Hydroxy-picolinic acid+15-Crown-5). The samples were desalted using the pipette tips ZipTip$_{c18}$: (Millipore) by washing with water and acetonitrile, or using MF™-membrane filters 0.025 µm VSWP (Millipore).

5.5 Synthesis of a 5 nt Oligonucleotide-PEG Conjugate Using a Cu/C Catalyst

Reaction of Oligo 2 with PEG-8-N$_3$

1 µl PEG-N$_3$ and Cu/C were added to 100 µl oligo 2 (1.6 nmol/µl→160 nmol$_{total}$) and put into thermal shaker for 2 h and 900 rpi at 25° C. Afterwards, the sample was diluted with 100 µl water and filtrated through Acrodisc 13 mm Syringe filter. The filters were washed with additional 100 µl water and the solution was used as it was for HPLC and MALDI Analysis. The product was additionally purified via RP-HPLC. The concentration was obtained using a nanophotometer.

Result: 93.8% recovery

Sequence:    3'-GATCU-X(PEG)$_8$NH$_2$

Amount*:     27 nmole; MW.: 2005 (1567 + 438).

*The amount was calculated from the concentration measured at 260 nm of 30 µL solution and it refers to the oligo concentration in solution (see 5.3).

where U---X is:

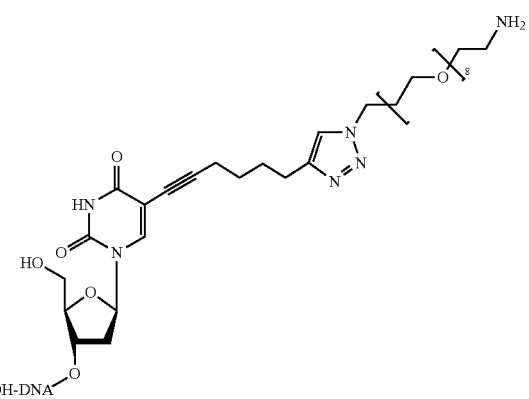

5.6 Synthesis of a 33 nt Oligonucleotide-PEG Conjugate Using a Cu/C Catalyst

Reaction of Oligo 3 with PEG-8-N$_3$

A modified 33-mer oligo (oligo 3) was used for this reaction. It contains a 5'-alkyne (C8-alkyne-dU), two Locked nucleosides (LNA bases) and a 3'-phosphate.

1 µl PEG-N$_3$ and Cu/C were added to 5 µl of oligo 3 (1.56 nmol/µl→7.8 nmol$_{total}$) and put into thermal shaker for 2 h and 900 rpi at 25° C. Afterwards, the sample was diluted with 100 µl water and filtrated through Acrodisc 13 mm Syringe filter. The filters were washed with additional 100 µl water and the solution was used as it was for HPLC and MALDI Analysis. The conjugate (R33-PEGS) was further purified via RP-HPLC yielding 176 pmol of pure product. The concentration was obtained using a nanophotometer.

Result: 80% recovery

Sequence: 3'-Phosphate-GACTCAAAGCGTAAGACCCTAAGAGA[T][C]TAAAU-X(PEG)$_8$NH$_2$

Amount*: O6 = 176 pmol; MW (g/mol).: 10825 (10387 + 438).

*The amounts were calculated from the concentrations measured at 260 nm and they refer to the oligo concentration in solution (see 5.3).

where U---X is:

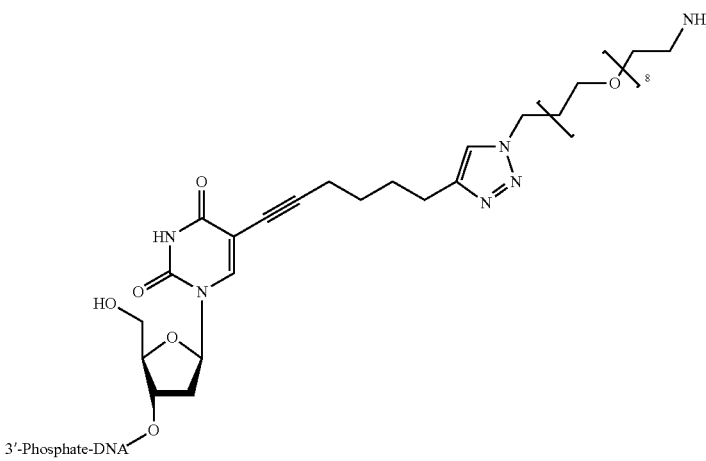

5.7 Synthesis of a 5 nt Oligonucleotide-Peptide Conjugate Using Cu/C Catalyst 75 μl Peptide-N$_3$ (1.2 mM→90 nmol$_{total}$) and Cu/C were added to 75 μl oligo 2 (1.6 nmol/μl→120 nmol$_{total}$) shaken for 2 h and 900 rpi at 25° C. The sample was then diluted with 100 μl water and filtrated through Acrodisc 13 mm Syringe filters. The filters were washed with additional 100 μl water and the resulting solution was used for MALDI, RP-HPLC analysis and purification. The concentration was measured at 280 nm using a Nanodrop.

Result: 97% recovery

Peptide-N$_3$ sequence = XYGQLRNSRAYGQLRNSRA-OH with X =

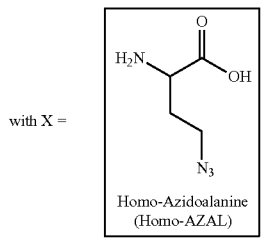

Homo-Azidoalanine (Homo-AZAL)

Sequence: 3'-GATCU--XYGQLRNSRAYGQLRNSRA-OH    Amount: 124 μg* (micrograms); 32.6 nmole; MW: 3803

*The amount was calculated from the concentration measured at 280 nm of 35 μL solution (see 5.3).

where U--X is:

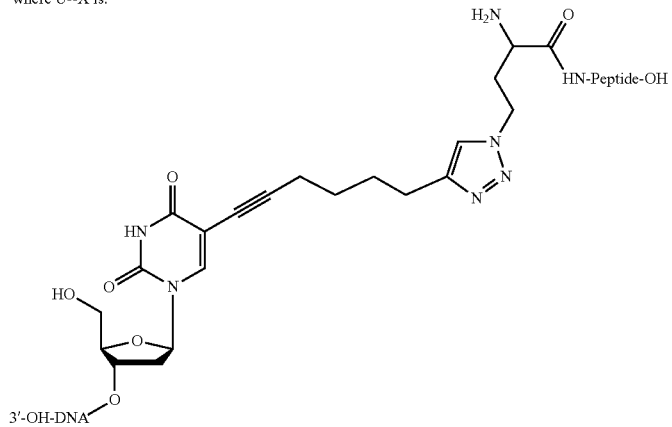

5.8 Conjugation of an Oligonucleotide with Biotin

Biotin-azide (0.4 μl, 326 g/mol, 20 equivalents) and Cu/C in EG (5 μL) were added to 3.8 μl Oligo 1 (6807.5 g/mol, 5 nmol/μl, 1 equivalent). Water (10 μl) was used as solvent. The reaction vial was shaken at 1000 rpi in a thermomixer at 60° C.

After 6 h the solution was diluted with 100 μl NaOAc (0.3 M) and filtered through a Nanosep spin column, which was previously washed with 100 μl H$_2$O and 100 μl DMSO/tBuOH (3:1). The filtered solution was further diluted with 100 μl NaOAc (0.3 M) followed by 1 ml cold EtOH/Et$_2$O (5%) for precipitation. The solution was centrifuged for 20 minutes at 6000 rpi. The organic phase was removed and 1 ml Et$_2$O was added. After centrifugation for 20 minutes at 6000 rpi the Et$_2$O was removed and the precipitate was dried at 37° C. and dissolved in 10 μl water.

Result: 44% recovery; 20% conversion.

5.9 Conjugation of an Oligonucleotide with FAM

5.9.1 Filtration with a PTFE Membrane

FAM (1 μl, 458 g/mol, 20 equivalents) and Cu/C in EG (5 μL) were added to 3.8 μl Oligo 1 (6807.5 g/mol, 5 nmol/μl, 1 equivalent). Water (20 μl) and 5 μl DMSO/tBuOH (3:1) were used as solvent. The reaction vial was shaken at 1000 rpi in a thermal shaker at 40° C.

After 3 h the solution was diluted with 200 μl NaOAc (0.3 M) and filtered through a 0.2 μm PTFE Membrane (VWR), which was previously washed with NaOAc (0.3 M), (2×100 μl). The filtered solution was washed again twice with 100 μl NaOAc (0.3 M) followed by 1 ml cold EtOH/Et$_2$O (5%) for precipitation. The solution was stored at −20° C. over night, centrifuged for 20 minutes at 6000 rpi. The organic phase was removed and 1 ml Et$_2$O was added. After centrifugation for 20 minutes at 6000 rpi the Et$_2$O was removed and the precipitate was dried at 37° C. and dissolved in 10 μl water.

Result: 65% recovery; 40% conversion

5.9.2 Filtration with a Nanosep Spin column

FAM (0.4 μl, 458 g/mol, 20 equivalents) and Cu/C in EG (5 μL) were added to Oligo 1 (3.8 μl, 6807.5 g/mol, 5 nmol/μl, 1 equivalent). Water (20 μl) was used as solvent. The reaction vial was shaken at 1000 rpi in a thermal shaker at 60° C.

After 6 h the solution was diluted with 100 μl NaOAc (0.3 M) and filtered through a Nanosep spin column, which was previously washed with 100 μl H$_2$O and 100 μl DMSO/tBuOH (3:1). The filtered solution was further diluted with 100 μl NaOAc (0.3 M) followed by 1 ml cold EtOH/Et$_2$O (5%) for precipitation. The solution was centrifuged for 20 minutes at 6000 rpi. The organic phase was removed and 1 ml Et$_2$O was added. After centrifugation for 20 minutes at 6000 rpi the Et$_2$O was removed and the precipitate was dried at 37° C. and dissolved in 10 μl water Result: 60% recovery; 70% conversion

5.10 Conjugation of an Oligonucleotide with a PEG-Linker

5.10.1 Reaction with $NH_2$-PEG-8 and Filtration with a PTFE Membrane $NH_2$-PEG-8 (0.4 µl, 438 g/mol, 20 equivalents) and Cu/C in EG (5 µL) were added to Oligo 1 (3.8 µl, 6807.5 g/mol, 5 nmol/µl, 1 equivalent). Water (10 µl) and DMSO/tBuOH (3:1) (5 µl) were used as solvent. The reaction vial was shaken at 1000 rpi in a thermal shaker at 40° C.

After 3 h the solution was diluted with 200 µl NaOAc (0.3 M) and filtered through a 0.2 µm PTFE Membrane (VWR), which was previously washed with NaOAc (0.3 M), (2×100 µl). The filtrate was washed twice with 100 µl NaOAc (0.3 M) followed by 1 ml cold EtOH/$Et_2O$ (5%) for precipitation. The solution was stored at −20° C. over night, centrifuged for 20 minutes at 6000 rpi. The organic phase was removed and 1 ml $Et_2O$ was added. After centrifugation for 20 minutes at 6000 rpi, the $Et_2O$ was removed and the precipitate was dried at 37° C. and dissolved in 10 µl water.

Result: 8.8% recovery; 100% conversion

5.10.2 Reaction with $NH_2$-PEG-8 and Filtration with a Nanosep Spin Column $NH_2$-PEG-8 (0.4 µl, 438 g/mol, 20 equivalents) and Cu/C in EG (5 µL) were added to Oligo 1 (3.8 µl, 6807.5 g/mol, 5 nmol/µl, 1 equivalent). Water (20 µl) was used as solvent. The reaction vial was shaken at 1000 rpi in a thermal shaker at 60° C.

After 6 h the solution was diluted with 100 µl NaOAc (0.3 M) and filtered through a Nanosep spin column, which was previously washed with 100 µl $H_2O$ and 100 µl DMSO/tBuOH (3:1). The filter was washed with 100 µl NaOAc (0.3 M) followed by 1 ml cold EtOH/$Et_2O$ (5%) for precipitation. The solution was centrifuged for 20 minutes at 6000 rpi. The organic phase was removed and 1 ml $Et_2O$ was added. After centrifugation for 20 minutes at 6000 rpi, the $Et_2O$ was removed and the precipitate was dried at 37° C. and dissolved in 10 µl water.

Result: 20% recovery; 100% conversion

5.10.3 Reaction with PEG-24 and Filtration with a PTFE Membrane

PEG-24 (10 µl, 1114 g/mol, 20 equivalents) and Cu/C in EG (5 µL) were added. to Oligo 1 (3.8 µl, 6807.5 g/mol, 5 nmol/µl, 1 equivalent). Water (10 µl) and 5 µl DMSO/tBuOH (3:1) (5 µl) were used as solvent. The reaction vial was shaken in a thermal shaker at 1000 rpi.

After 3 h the solution was diluted with 200 µl NaOAc (0.3 M), filtered through a 0.2 µm PTFE Membrane (VWR), which was previously washed with NaOAc (0.3 M), (2×100 µl). The filtrate was washed twice with 100 µl NaOAc (0.3 M) followed by 1 ml cold EtOH/$Et_2O$ (5%) for precipitation. The solution was stored at −20° C. over night, centrifuged for 20 minutes at 6000 rpi. The organic phase was removed and 1 ml $Et_2O$ was added. After centrifugation for 20 minutes at 6000 rpi, the $Et_2O$ was removed and the precipitate was dried at 37° C. and dissolved in 10 µl water.

Result: 16% recovery; 80% conversion

REFERENCES

[1] R. Huisgen, 1,3-Dipolar Cycloaddition Chemistry (Ed.: A. Padwa), Wiley, New York, 1984.

[2] K. B. Sharpless, V. V. Fokin, L. G. Green, V. V. Rostovtsev, *Angew. Chem.* 2002, 114, 2708; *Angew. Chem. Int. Ed.* 2002, 41, 2596.

[3] M. Meldal, C. Christensen, C. W. Tornoe, *J. Org. Chem.* 2002, 67, 3057.

[4] J. H. Maarseveen, H. Hiemstra, V. D. Bock, Eur. *J. Org. Chem.* 2006, 51

[5] a) K. B. Sharpless, V. V. Fokin, V. V. Rostovtsev, L. Noodleman, R. Hilgraf, T. Lovell, F. Himo, *J. Am. Chem. Soc.* 2005, 127, 210; b) C. J. Hawker, T. P. Russell, P. Wu, V. V. Fokin, E. Drockenmuller, K. Schleicher, M. Malkoch, *Macromolecules* 2005, 38, 3663.

[6] a) P. Gmeiner, H. Hubner, S. Lober, P.-R. Loaiza, *J. Comb. Chem.* 2006, 8, 252; b) M. G. Finn, Q. Wang, J. Kuzelka, S. Punna, *Angew. Chem.* 2005, 117, 2255; *Angew. Chem. Int. Ed.* 2005, 44, 2215.

[7] a) C. Girard, E. Onen, M. Aufort, S. Beauviere, E. Samson, J. Herscovici, *Org. Lett.* 2006, 8, 1689; b) G. Rothenberg, J.-V. Maarseveen, L. D. Pachon, *Adv. Synth. Catal.* 2005, 347, 811; see also: A. Ponti, N. Santo, G. Marinoni, C. L. Bianchi, G. Molteni, *New J. Chem.* 2006, 30, 1137.

[8] Aldrich Catalogue, #278092. Darko K B, Wet Powder, 100 mesh, contains less than 30% water.

[9] B. H. Lipshutz, B. A. Frieman, A. E. Tomaso, *Angew. Chem.* 2006, 118, 1281; *Angew. Chem. Int. Ed.* 2006, 45, 1259.

[10] T. Tsoncheva, S. Vankova, D. Mehandjiev, *Fuel* 2003, 82, 755.

[11] V. V. Fokin, K. B. Sharpless, R. Hilgraf, T. R. Chan, *Org. Lett.* 2004, 6, 2853.

[12] M. G. Finn, V. V. Fokin, V. O. Rodionov, *Angew. Chem.* 2005, 117, 2250; *Angew. Chem. Int. Ed.* 2005, 44, 2210.

[13] M. R. Ghadiri, C. D. Stout, W. S. Home, *J. Am. Chem. Soc.* 2003, 125, 9372.

[14] C-H. Wong, J. C. Paulson, O. Blixt, M. C. Bryan, F. Fazio, *J. Am. Chem. Soc.* 2002, 124, 14397.

[15] For a recent article that describes use of copper(II) salts to catalyze Click cycloadditions in water, see: M. L. Kantam, K. Rajgopal, K. R. Reddy, *Synlett* 2006, 957-959.

[16] Gramlich, P. M. A.; Wirges, C. T.; Manetto, A.; Carell, T., Postsynthetic DNA Modification through the Copper-Catalyzed Azide-Alkyne Cycloaddition Reaction. *Angew. Chem. Int. Ed.,* 2008, 47, 8350-8358.

[17] C. J. Burrows, J. G. Muller, *Chem. Rev.* 1998, 98, 1109-1152.

[18] S. Thyagarajan, N. N. Murthy, A. A. Narducci Sarjeant, K. D. Karlin, S. E. Rokita, *J. Am. Chem. Soc.* 2006, 128, 7003-7008.

[19] H. Lipshutz, B. R. Taft, *Angew. Chem. Int. Ed.,* 2006, 45, 8235-8238.

[20] D. Urankar, J. Košmrli, J. Comb. Chem. 2008, 10, 981-988.

[21] H. Sharghi, R. Khalifeh, M. M. Doroodmand, Adv. Synth. Catal. 2009, 351, 207-218

[22] J. F. Lutz, Z. Zarafshani, Adv. Drug Deliv. Rev. 2008, 60, 958-970.

[23] WO 2006/11761

[24] WO 2008/052775

The invention claimed is:

1. A method of coupling a first molecule to a second molecule by a Click reaction, comprising contacting the first molecule comprising a first Click functional group, which is an alkyne group, and the second molecule comprising a second complementary Click functional group, which is an azide group capable of reacting with the first Click-functional group by a Click reaction, in the presence of a heterogeneous Cu—C catalyst under conditions wherein the Click reaction between the first and second molecule occurs wherein one of the first and second molecules is immobilized on a dry solid carrier thereby pre-impregnating the solid carrier, and contacting the dry solid carrier pre-impregnated with one of the first and second molecules with a liquid medium comprising the other molecule, wherein the solid carrier is the heterogeneous Cu—C catalyst.

2. The method of claim 1, wherein one of the first and second molecules is a biomolecule.

3. The method of claim 1, wherein the first molecule is a biomolecule selected from the group consisting of nucleosides, nucleotides, nucleic acids, amino acids, peptides, saccharides and lipids.

4. The method of claim 3, wherein the biomolecule is a nucleic acid.

5. The method of claim 1, wherein the second molecule is selected from the group consisting of
  (i) a reporter molecule, optionally a dye;
  (ii) an affinity molecule;
  (iii) a solid phase;
  (iv) a biomolecule, optionally a protein or a lipid;
  (v) a linker or a spacer, optionally comprising an aliphatic or cycloaliphatic group, an aromatic or heteroaromatic group, an alkene group, an alkyne group, and/or a polymeric group, optionally a polyethylene glycol group; and
  (vi) a pharmaceutical compound or group, a photoactive group, a redox active group, and/or a recognition site.

6. The method of claim 1, wherein the Click reaction is carried out in the presence of a molecule able to interact with the heterogeneous system increasing the rate of the Click reaction.

7. The method of claim 6, wherein the molecule able to interact with the heterogenous system increasing the rate of the click reaction is an amine.

8. The method of claim 7, wherein the amine is present in amounts of up to 10% (v/v), 1% (v/v) or 0.1% (v/v).

9. The method of claim 7, wherein the amine is a primary, secondary or tertiary amine optionally having an aromatic, heteroaromatic, aliphatic, cycloaliphatic, unsaturated or fully saturated backbone.

10. The method of claim 7, wherein the amine is triethylamine.

11. The method of claim 1, wherein the reaction has a temperature is between about 4 and about 80° C.

12. The method of claim 11, wherein the reaction temperature is between about 10 and about 40° C.

13. The method of claim 11, wherein the reaction has a reaction time is between about 1 min and about 8 h.

14. The method of claim 13, wherein the reaction time is between about 1 min and about 10 min.

15. The method of claim 13, wherein the reaction time is between about 2 min and about 5 min.

16. The method of claim 13, wherein the reaction time is between about 10 min and 8 h.

17. The method of claim 13, wherein the reaction volume is from about 0.1 to about 1000 µl.

18. The method of claim 1, wherein the reaction is carried out in a pipette tip, a spin column or a syringe.

19. The method of claim 1, further comprising a separation/purification step.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: Oligo 1
<220> FEATURE:
<221> NAME/KEY: misc_feature
<222> LOCATION: (21)..(21)
<223> OTHER INFORMATION: Z attached 3' to this residue; Z = C8dC(X),
      wherein X is as defined in the description

<400> SEQUENCE: 1
cgcgtatcgc tatcgctatg g                                              21

<210> SEQ ID NO 2
<211> LENGTH: 4
<212> TYPE: DNA
<213> ORGANISM: Artificial
<220> FEATURE:
<223> OTHER INFORMATION: Oligo 2
<220> FEATURE:
<221> NAME/KEY: misc_feature
<222> LOCATION: (1)..(1)
<223> OTHER INFORMATION: Z attached 5' to this residue; Z = C8dC(X),
      wherein X is as defined in the description

<400> SEQUENCE: 2 ctag                                                                  4

<210> SEQ ID NO 3
<211> LENGTH: 32
<212> TYPE: DNA
<213> ORGANISM: Artificial
<220> FEATURE:
<223> OTHER INFORMATION: Oligo 3
<220> FEATURE:
<221> NAME/KEY: misc_feature
<222> LOCATION: (1)..(1)
<223> OTHER INFORMATION: Z attached 5' to this residue; Z = C8dC(X),
      wherein X is as defined in the description
<220> FEATURE:
<221> NAME/KEY: modified_base
<222> LOCATION: (5)..(5)
<223> OTHER INFORMATION: modified (LNA) nucleotide
<220> FEATURE:
<221> NAME/KEY: modified_base
<222> LOCATION: (6)..(6)
<223> OTHER INFORMATION: modified (LNA) nucleotide
<220> FEATURE:
<221> NAME/KEY: modified_base
<222> LOCATION: (32)..(32)
<223> OTHER INFORMATION: phosphate at 3'

<400> SEQUENCE: 3
aaatctagag aatcccagaa tgcgaaactc ag                                  32

<210> SEQ ID NO 4
<211> LENGTH: 19
<212> TYPE: PRT
<213> ORGANISM: Artificial
<220> FEATURE:
<223> OTHER INFORMATION: Peptide-N3 sequence
<220> FEATURE:
<221> NAME/KEY: MISC_FEATURE
<222> LOCATION: (1)..(1)
<223> OTHER INFORMATION: X = Homo-Azidoalanine (Homo-AZAL)

<400> SEQUENCE: 4

```
Xaa Tyr Gly Gln Leu Arg Asn Ser Arg Ala Tyr Gly Gln Leu Arg Asn
1               5                   10                  15
Ser Arg Ala
```